(12) United States Patent
Richards et al.

(10) Patent No.: US 10,013,531 B2
(45) Date of Patent: Jul. 3, 2018

(54) CONTEXT BASED AUGMENTED REALITY

(71) Applicant: Accenture Global Service Limited, Dublin (IE)

(72) Inventors: Brian Richards, Chicago, IL (US); Brent Robert Blum, San Francisco, CA (US); Timothy Li, Milpitas, CA (US); Byron John Schmidt, Calgary (CA); Amjad-Ali Khoja, Sugar Land, TX (US)

(73) Assignee: ACCENTURE GLOBAL SERVICES LIMITED, Dublin (IE)

( * ) Notice: Subject to any disclaimer, the term of this patent is extended or adjusted under 35 U.S.C. 154(b) by 0 days.

(21) Appl. No.: 14/653,208

(22) PCT Filed: Dec. 20, 2013

(86) PCT No.: PCT/US2013/077136
§ 371 (c)(1),
(2) Date: Jun. 17, 2015

(87) PCT Pub. No.: WO2014/100688
PCT Pub. Date: Jun. 26, 2014

(65) Prior Publication Data
US 2015/0339453 A1    Nov. 26, 2015

Related U.S. Application Data

(60) Provisional application No. 61/739,808, filed on Dec. 20, 2012.

(51) Int. Cl.
*G06F 19/00*    (2018.01)
*G06T 11/00*    (2006.01)
(Continued)

(52) U.S. Cl.
CPC .......... *G06F 19/3418* (2013.01); *G06T 11/00* (2013.01); *G06T 19/006* (2013.01);
(Continued)

(58) Field of Classification Search
CPC ............. G06F 19/3418; G06F 19/3425; G06F 17/5009; G06T 19/006
(Continued)

(56) References Cited

U.S. PATENT DOCUMENTS

2008/0020361 A1*    1/2008    Kron ...................... G09B 23/28
                                                                  434/262
2009/0167787 A1*    7/2009    Bathiche ................. A63F 13/10
                                                                  345/633

(Continued)

FOREIGN PATENT DOCUMENTS

EP    2521109 A1    11/2012
WO    WO-2011/160076 A2    12/2011

OTHER PUBLICATIONS

International Search Report and Written Opinion dated Jun. 9, 2015, issued on PCT Patent Application No. PCT/US2013/077136 dated Dec. 20, 2013, The European Patent Office.

(Continued)

*Primary Examiner* — Samantha (Yuehan) Wang
(74) *Attorney, Agent, or Firm* — Mannava & Kang, P.C.

(57) ABSTRACT

Context based AR may include receiving a first wireless signal from a pair of context based AR glasses worn by a user. The context based AR glasses may include a display viewable by the user and a camera to image an object viewed by the user. The image of the object may be analyzed, and compared to images of objects stored in a database that includes information associated with the images of the objects. Based on a match, the object viewed by the user may be identified. Based on collaboration of the user with (Continued)

personnel disposed remotely from the user, and the identified object, a second wireless signal may be sent to the pair of context based AR glasses to provide information related to the collaboration, and to further superimpose the information associated with the identified object adjacent to and/or on top of the object viewed by the user.

20 Claims, 20 Drawing Sheets

(51) Int. Cl.
*G06T 19/00* (2011.01)
*G16H 80/00* (2018.01)
*A61B 90/00* (2016.01)

(52) U.S. Cl.
CPC .............. *G16H 80/00* (2018.01); *A61B 90/37* (2016.02); *A61B 2090/365* (2016.02)

(58) Field of Classification Search
USPC ......................................................... 345/633
See application file for complete search history.

(56) References Cited

U.S. PATENT DOCUMENTS

| | | | | |
|---|---|---|---|---|
| 2009/0270678 | A1* | 10/2009 | Scott | A61B 1/00009 600/109 |
| 2011/0153341 | A1* | 6/2011 | Diaz-Cortes | G06F 19/322 705/2 |
| 2013/0009993 | A1* | 1/2013 | Horseman | G06F 19/3418 345/633 |
| 2013/0069985 | A1* | 3/2013 | Wong | G02B 27/017 345/633 |
| 2013/0345718 | A1* | 12/2013 | Crawford | A61B 17/025 606/130 |
| 2014/0139405 | A1* | 5/2014 | Ribble | G06F 19/327 345/8 |

OTHER PUBLICATIONS

Nilsson et al., "Using AT to support cross-organisational collaboration in dynamic tasks", IEEE International Symposium on Mixed and Augmented Reality, Oct. 19-22, 2009, Orlando, FL, USA, pp. 1-10.
Partial International Search dated Apr. 1, 2015, issued on PCT Patent Application No. PCT/US2013/077136 dated Dec. 20, 2013, The European Patent Office.

* cited by examiner

CONTEXT BASED AUGMENTED REALITY

CROSS-REFERENCE TO RELATED APPLICATION(S)

This application is a national stage filing under 35 U.S.C 371 of PCT application number PCT/US2013/077136, having an international filing date of Dec. 20, 2013, which claims the benefit of Provisional Patent Application Ser. No. 61/739,808, filed Dec. 20, 2012, the disclosures of which are expressly incorporated herein by reference in their entireties.

INCORPORATION BY REFERENCE

U.S. Pat. No. 7,050,078 (App. Ser. No. 10/326,158), Titled "Arbitrary Object Tracking Augmented Reality Applications," and U.S. Pat. No. 7,372,451 (App. Ser. No. 10/492,437), Titled "Industrial Augmented Reality," and U.S. Patent Application Publication No. 2011/0037571 (App. Ser. No. 12/847,718), Titled "System for Relative Positioning of Access Points in a Real Time Locating System," are commonly owned and related to the present application, and are incorporated by reference in their entireties.

BACKGROUND

Augmented reality (AR) typically includes a live, direct or indirect, view of a physical, real-world environment whose elements are augmented (e.g., supplemented) by computer-generated sensory input. The computer-generated sensory input typically includes sound, video, graphics, or global positioning system (GPS) data. AR can enhance a user's perception of reality.

BRIEF DESCRIPTION OF DRAWINGS

Features of the present disclosure are illustrated by way of examples shown in the following figures. In the following figures, like numerals indicate like elements, in which.

DETAILED DESCRIPTION

Figure 1:
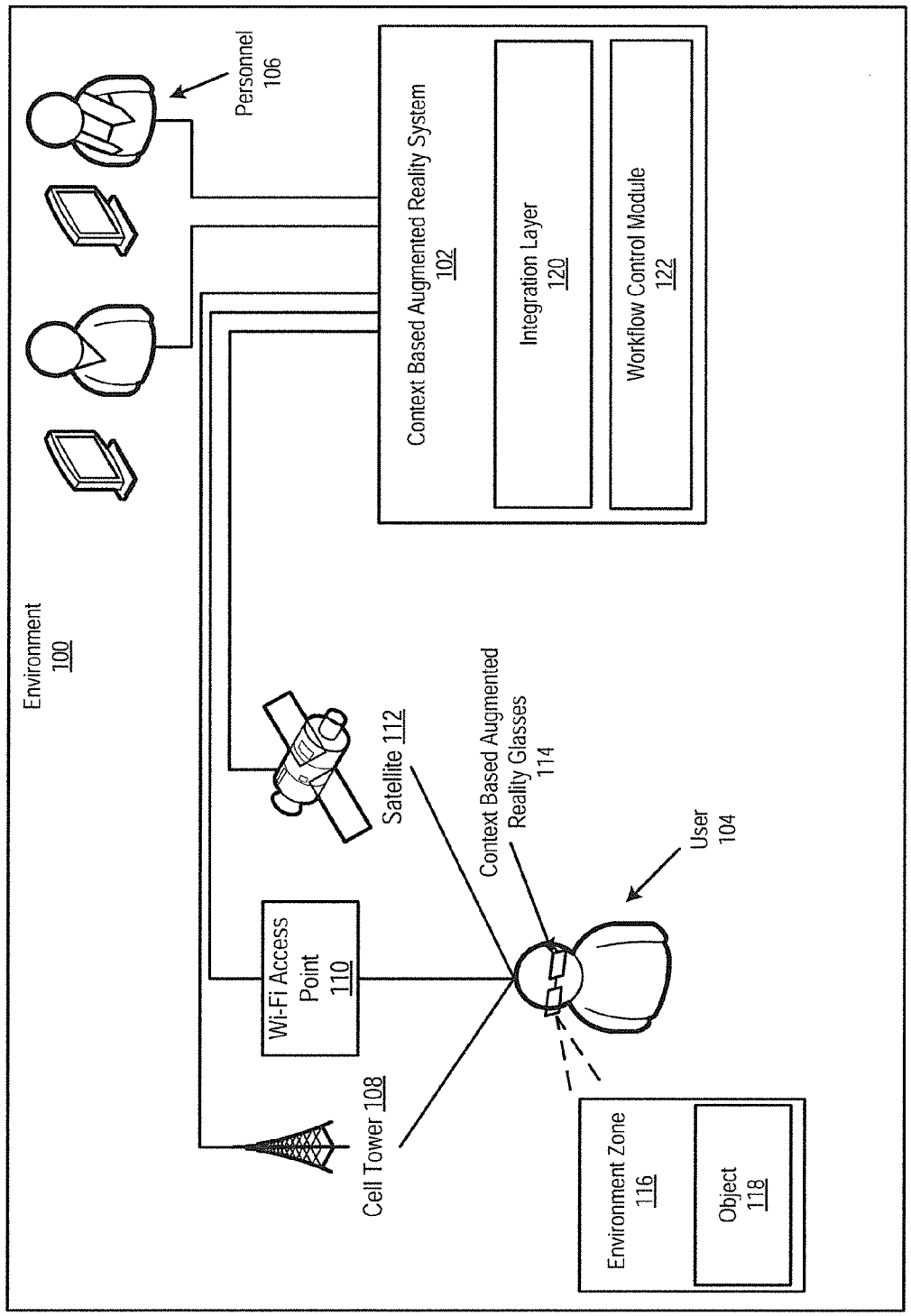
FIG. 1 illustrates an environment including a context based augmented reality (AR) system, according to an example of the present disclosure.

For simplicity and illustrative purposes, the present disclosure is described by referring mainly to examples thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Unlike virtual reality (VR) which replaces the real world with a simulated one, augmented reality (AR) typically includes the real-time overlay of virtual data, images, and videos onto live video feeds. For AR, the base layer is typically real and may include, for example, a live video feed, or in the case of head-mounted displays, a user's own vision. According to examples disclosed herein, a context based AR system and a method for context based AR are disclosed herein, and may generally provide for implementation of AR in a variety of fields. For example, the system and the method for context based AR disclosed herein may provide for a user, such as, for example, a field technician, an EMT, a physician, etc., to collaborate with remote experts or other personnel. The collaboration may be performed, for example, in the field of oil and gas, and other such fields, where field workers and other personnel are required to wear safety glasses when in any high risk location. Such safety glasses may be implemented as context based AR glasses as disclosed herein. According to another example, the collaboration may be performed in the medical and other such fields, where EMTs and/or physicians may wear the context based AR glasses as disclosed herein to perform a variety of tasks.

The system and method for context based AR disclosed herein may provide, for example, collaboration with remote experts, identification and avoidance of safety hazards, access to maintenance information, and training.

With respect to collaboration, the system and method disclosed herein may provide, for example, audio and video capabilities with remote experts, audio search of knowledge repositories, and remote collaboration with instructors. With respect to identification and avoidance of safety hazards, the system and method disclosed herein may provide, for example, go and no-go zone identification, safety alerts, and lock-out and tag-out operations. With respect to access to maintenance information, the system and method disclosed herein may provide, for example, maintenance history and checklist analysis, and step-by-step repair guidance. With respect to training, the system and method disclosed herein may provide, for example, training videos overlaid on actual equipment and environment, and customizable training.

According to an example disclosed herein, the context based AR system may include a processor, and a video analytics and computer vision module that is executed by the processor to receive a first wireless signal from a pair of context based AR glasses worn by a user. The context based AR glasses may include a display viewable by the user and a camera to image an object viewed by the user. The video analytics and computer vision module may analyze the image of the object viewed by the user, compare the image of the object viewed by the user to a plurality of images of objects stored in a database including information associated with the plurality of images of the objects, and based on a match of the image of the object viewed by the user to one of the plurality of images of the objects stored in the database, identify the object viewed by the user. A collaboration integration module that is executed by the processor may implement collaboration of the user with personnel disposed remotely from the user. Based on the collaboration and the identified object, the collaboration integration module may send a second wireless signal to the pair of context based AR glasses worn by the user to provide information related to the collaboration, and to further superimpose the information associated with the identified object adjacent to and/or on top of the object viewed by the user.

According to an example disclosed herein, the method for context based AR may include receiving, by a video analytics and computer vision module including a processor, a first wireless signal from a pair of context based AR glasses worn by a user. The method may further include analyzing, by the video analytics and computer vision module, the image of the object viewed by the user, comparing the image of the object viewed by the user to a plurality of images of objects stored in a database including information associated with the objects, and identifying the object viewed by the user based on a match of the image of the object viewed by the user to one of the plurality of images of the objects stored in the database. The method may further include allowing, by a collaboration integration module including a processor, collaboration of the user with personnel disposed remotely from the user. The method may further include sending, by the collaboration integration module, based on the collaboration and the identified object, a second wireless signal to the pair of context based AR glasses worn by the user to provide information related to the collaboration, and to further superimpose the information associated with the identified object adjacent to and/or on top of the object viewed by the user.

According to an example disclosed herein, a non-transitory computer readable medium having stored thereon machine readable instructions for context based AR is disclosed herein. The machine readable instructions, that when executed, cause a computer system to receive, by a processor, a first wireless signal indicative of a location of a pair of context based AR glasses worn by a user. The machine readable instructions, that when executed, further cause the computer system to analyze the first wireless signal to determine the location of the pair of context based AR glasses worn by the user, compare the location of the pair of context based AR glasses worn by the user to a plurality of locations stored in a database including information associated with the locations, and identify the location of the pair of context based AR glasses worn by the user based on a match of the location of the pair of context based AR glasses worn by the user to one of the plurality of locations stored in the database. The machine readable instructions, that when executed, further cause the computer system to allow collaboration of the user with personnel disposed remotely from the user, and send, based on the collaboration and the identified location, a second wireless signal to the pair of context based AR glasses worn by the user to provide information related to the collaboration and to further superimpose the information associated with the location adjacent to and/or on top of an environment viewed by the user.

Applications of the context based AR system and the method for context based AR may include, for example, hands-free collaboration by offshore personnel that collaborate in real-time with an onshore expert to fix a defect with a blowout preventer. Another application may include training of a user (e.g., a drilling engineer) of the context based AR glasses for an offshore platform by using actual schematics of a platform with the rest of the equipment virtually generated so that the training is specific to user's job location. Another application may include how a user (e.g., a technician) of the context based AR glasses may replace a worn-out pump casing on a real mud pump that the user has never worked on before. Generally, examples of the application of the context based AR system and the method for context based AR may include allowing users (e.g., field workers) in high risk and dangerous locations to collaborate with remote experts, identify and avoid safety hazards, access maintenance information, and receive training.

The context based AR system and the method for context based AR disclosed herein provide a technical solution to technical problems related, for example, to workflow control, collaboration between employees disposed at job sites and remote experts, training of employees, maintenance of equipment, and employee safety. In many instances, efficiency of performance of various tasks can be limited, for example, due to the lack of information available to individuals at job sites. The system and method disclosed herein provide the technical solution of receiving a first wireless signal from a pair of context based AR glasses worn by a user. An image of an object viewed by the user may be analyzed, and compared to a plurality of images of objects stored in a database including information associated with the objects. The object viewed by the user may be identified based on a match of the image of the object viewed by the user to one of the plurality of images of the objects stored in the database. The system and method disclosed herein may allow for collaboration of the user, by the context based AR glasses, with personnel disposed remotely from the user. Based on the collaboration and the identified object, a second wireless signal may be sent to the pair of context based AR glasses worn by the user to provide information related to the collaboration, and to further superimpose the information associated with the identified object adjacent to and/or on top of the object viewed by the user.

FIG. 1 illustrates an environment 100 including a context based AR system 102, according to an example of the present disclosure. The environment 100 may include a user 104, such as, for example, a field technician, an EMT, a physician, etc., to collaborate with remote experts or other personnel 106. The user 104 may communicate with the personnel 106 via the context based AR system 102. The intermediate connection to the context based AR system 102 may be provided, for example, wirelessly via sources, such as, for example, cell towers 108, Wi-Fi access points 110, and/or satellite based communication 112. Alternatively or additionally, the intermediate connection to the context based AR system 102 may be implemented by downloading data to a portable device (e.g., a smart phone, tablet, or other portable computing device) in which operations such as the identification of an object and transmission of the image for superimposition are performed by the portable device. The user 104 may use context based AR glasses 114 to ascertain and display real-time virtual data, images, and videos onto the user's own vision of an environment zone 116 including an object 118. The context based AR glasses 114 may be implemented as a set of glasses that are worn by the user 104, or alternatively, implemented as a mobile device having a display and a camera, such as smart phones or tablets with cameras. The context based AR system 102 may generally include an integration layer 120 to provide integration of the context based AR glasses 114 with a variety of vendor based applications. For example, the integration layer 120 may provide integration of the context based AR glasses 114 with GOOGLE, MICROSOFT, APPLE, etc., based applications. A workflow control module 122 may control operation of the context based AR system 102 to provide, for example, collaboration for the user 104 with the personnel 106 based on the user's vision of the environment zone 116 including the object 118. The workflow control module 122 may further control operation of the context based AR system 102 to provide video analytics and computer vision support for the user 104 and the personnel 106. The workflow control module 122 may also control operation of the context based AR system 102 to provide audio search capabilities for the user 104 and the personnel 106.

As described herein, the modules and other elements of the context based AR system 102 may be machine readable instructions stored on a non-transitory computer readable medium. In addition, or alternatively, the modules and other elements of the context based AR system 102 may be hardware or a combination of machine readable instructions and hardware.

Figure 2A:
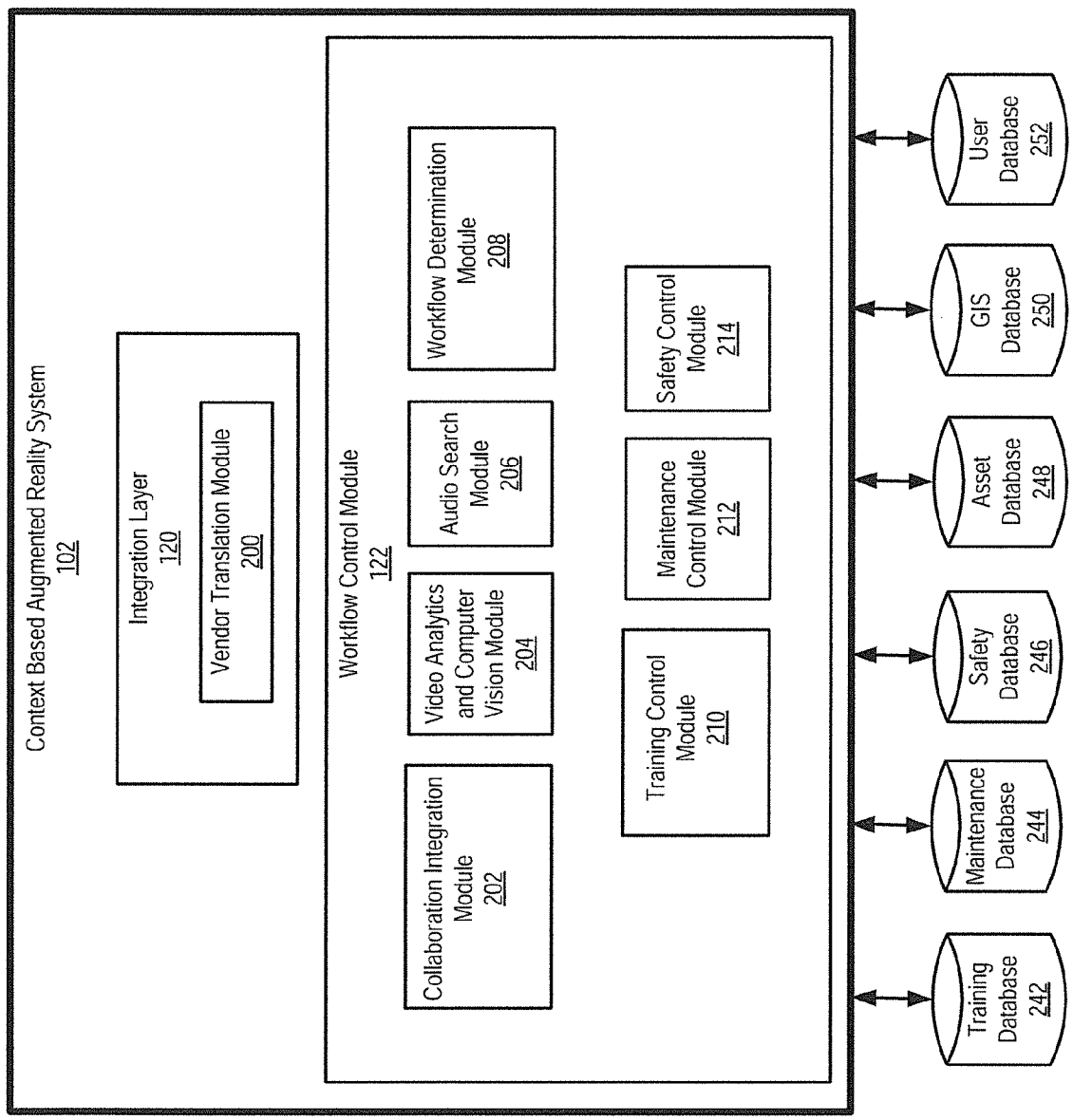
FIGS. 2A and 2B illustrate a detailed architecture of the context based AR system of FIG. 1, according to an example of the present disclosure.
Figure 2B:
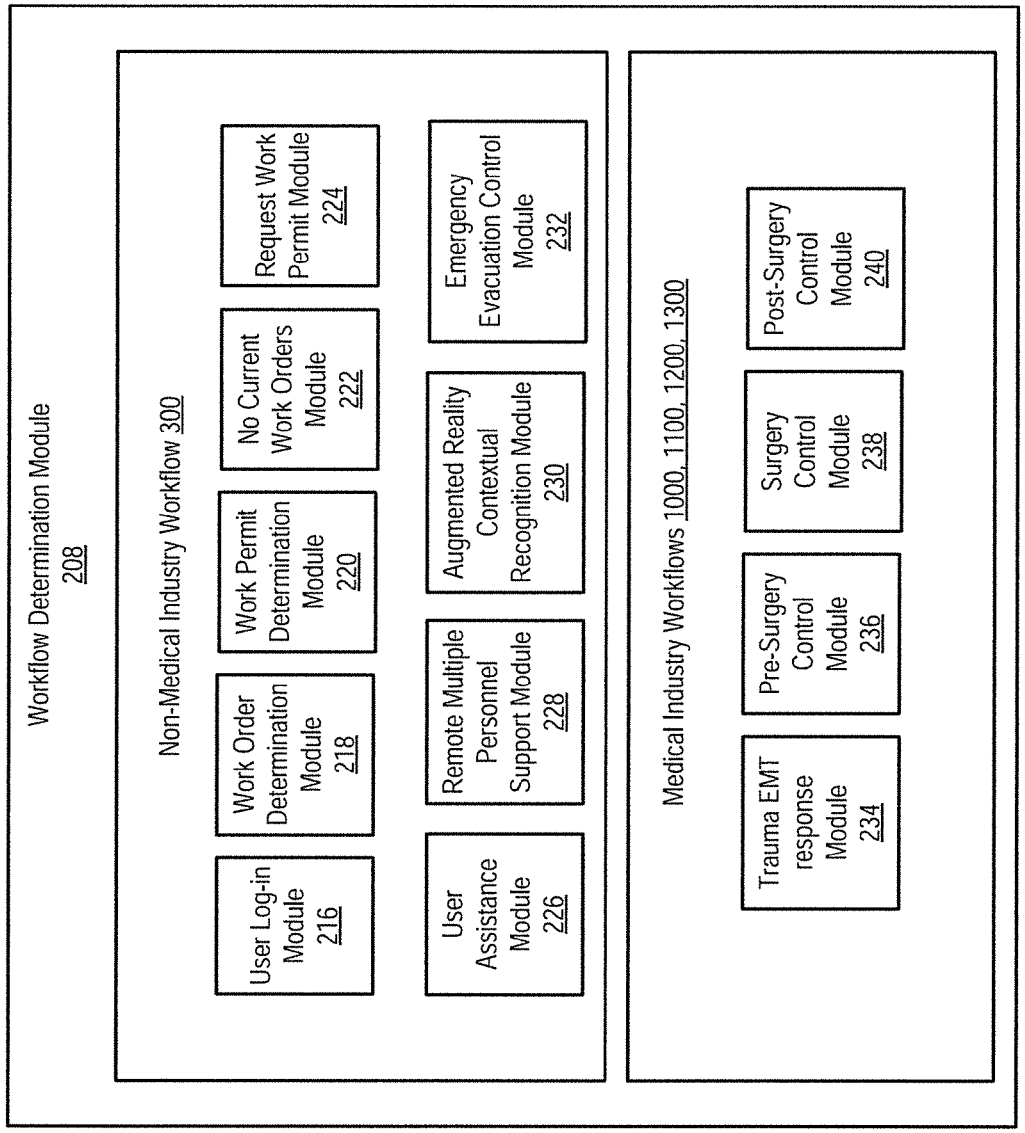

FIGS. 2A and 2B illustrate a detailed architecture of the context based AR system 102 of FIG. 1, according to an example of the present disclosure. The context based AR system 102 may include the integration layer 120 to provide integration of the context based AR glasses 114 with a variety of vendor based applications. For example, the integration layer 120 may provide integration of the context based AR glasses 114 with GOOGLE, MICROSOFT, APPLE, etc., based applications, via vendor translation module 200. A different vendor translation module 200 may be provided for each different vendor based application.

The context based AR system 102 may include the workflow control module 122 including a collaboration integration module 202 to control operation of the context based AR system 102 to provide, for example, collaboration for the user 104 with the personnel 106 based on the user's vision of the environment zone 116 including the object 118. The workflow control module 122 may include a video analytics and computer vision module 204 to control operation of the context based AR system 102 to provide video analytics and computer vision support for the user 104 and the personnel 106. An audio search module 206 may control operation of the context based AR system 102 to provide audio search capabilities for the user 104 and the personnel 106. A workflow determination module 208 may determine a type of workflow involving the user 104, the personnel 106, and the context based AR system 102. For example, the workflow determination module 208 may determine a general non-medical industry workflow, illustrated herein as workflow 300 with reference to FIG. 3, involving the user 104 that is to perform a given work order. Alternatively or additionally, the workflow determination module 208 may determine a medical industry workflow, illustrated herein as workflows 1000, 1100, 1200, and 1300, respectively, with reference to FIGS. 10, 11, 12A, 12B, and 13. Similarly, the workflow determination module 208 may determine other types of workflows that may be implemented by the context based AR system 102.

A training control module 210 may implement training functionality for the user 104, for example, to train the user 104 on how to work with or maintain complex equipment in dangerous environments. A maintenance control module 212 may implement maintenance functionality for the user 104, for example, to use the context based AR glasses 114 to look at a piece of equipment or machinery, have that equipment recognized using computer vision, and to provide the user 104 with a checklist of activities to perform a particular maintenance activity and/or augment the user's view with computer drawings and designs that show how to perform a particular maintenance activity. A safety control module 214 may implement safety functionality for the user 104, for example, to geographically track the user 104 via the context based AR glasses 114, and alert the user 104 when the user has moved into a dangerous location or an unauthorized area.

Referring to FIG. 2B, with respect to the non-medical industry workflow 300, the workflow determination module 208 may include a user log-in module 216 that may be used by the user 104 to log-in to the context based AR system 102. A work order determination module 218 may determine and assign an appropriate work order to the user 104 as described in further detail with reference to FIG. 4. A work permit determination module 220 may ascertain an appropriate work permit for the user 104 based on the work order. A no current work orders module 222 may implement a no current work orders logic 400 of FIG. 4 to generally scan work that has been assigned to the user 104, and to determine work that meets the user's skills and availability. A request work permit module 224 may implement the request work permit logic 500 of FIG. 5. A user assistance module 226 may implement the user assistance logic 600 of FIG. 6. A remote multiple personnel support module 228 may implement the remote multiple personnel support logic 700 of FIG. 7. An AR contextual recognition module 230 may implement the AR contextual recognition logic 800 of FIG. 8. An emergency evacuation control module 232 may implement the emergency evacuation logic 900 of FIG. 9.

Figure 10:
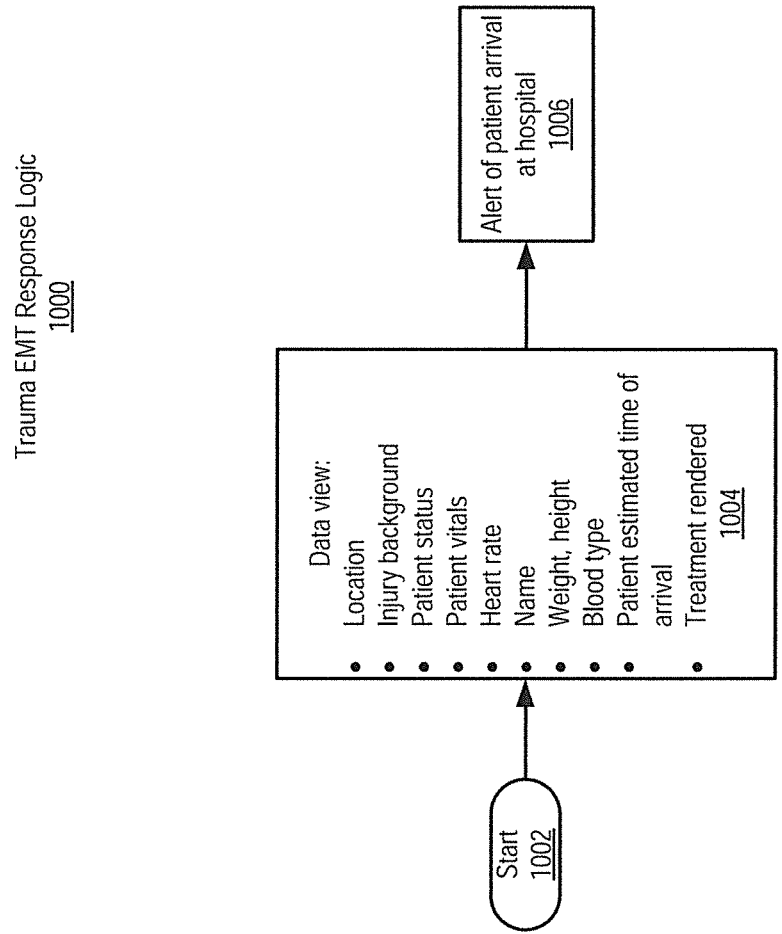
FIG. 10 illustrates a flowchart of a trauma emergency medical technician (EMT) response logic, according to an example of the present disclosure.

With respect to the medical industry workflows 1000, 1100, 1200, and 1300, the workflow determination module 208 may include a trauma emergency medical technician (EMT) response module 234 to implement a trauma EMT response logic 1000 of FIG. 10. A pre-surgery control module 236 may implement the pre-surgery logic 1100 of FIG. 11. A surgery control module 238 may implement the surgery logic 1200 of FIGS. 12A and 12B. A post-surgery control module 240 may implement the post-surgery logic 1300 of FIG. 13.

Referring to FIGS. 1 and 2A, the context based AR system 102 may communicate with a training database 242, maintenance database 244, safety database 246, asset database 248, geographic information system (GIS) database 250, and user database 252. The training database 242, maintenance database 244, and safety database 246 may include information related, respectively, to training, maintenance, and safety aspects of the user 104. The asset database 248 may include information related to management of business operations and customer relations. The GIS database 250 may include information related to capture, storage, manipulation, analysis, management, and presentation of geographical data related to the user 104 and the context based AR glasses 114. The user database 252 may include information related, for example, to qualifications, history, current status, etc., of the user 104. The operation of the context based AR system 102 in conjunction with the databases 242-252 is described in further detail herein with reference to FIGS. 3A-13.

Referring to FIG. 1, the context based AR glasses 114 may generally function as a head mounted display unit that provides graphic overlays. The context based AR glasses 114 may be tracked by the context based AR system 102 that augments the natural view of the user 104, for example, with text, labels, arrows, and animated sequences designed to facilitate task comprehension, location, and execution. The context based AR glasses 114 may use wireless infrastructure, such as, for example, the cell towers 108, Wi-Fi access points 110, and/or satellite based communication 112, to connect to the databases 242-252. The workflow control module 122 may integrate the capabilities of the collaboration integration module 202, the video analytics and computer vision module 204, the audio search module 206, the workflow determination module 208, the training control module 210, the maintenance control module 212, and the safety control module 214.

Referring to FIGS. 1 and 2A, the collaboration integration module 202 may generally provide for audio and video integration of the user 104 wearing the context based AR glasses 114 with the remote personnel 106. The audio and video integration may be implemented in conjunction with the video analytics and computer vision module 204, and the audio search module 206. The collaboration integration module 202 may provide for remote collaboration of the user 104 with the personnel 106. These aspects related to the collaboration integration module 202 may generally provide for decreased usage of users 104 (e.g., technicians) in dangerous and/or expensive locations, and/or improved accessibility by the users 104. Based on the audio and video capabilities of the context based AR glasses 114, the collaboration integration module 202 may provide for the personnel 106 to see and hear what the user 104 wearing the context based AR glasses 114 is seeing and hearing, and communicate with the user 104. The collaboration integration module 202 may thus provide for a remote user 104 to connect with the personnel 106 (e.g., experts) who are in safer and/or lower cost locations to guide the user 104, for example, thru maintenance activities, provide checklists in their context based AR glasses 114, and use voice search to browse enterprise knowledge repositories, such as the databases 242-252.

The training control module 210 may implement training functionality for the user 104, for example, to train the user 104 on how to work with or maintain complex equipment in dangerous locations. The training control module 210 may operate in conjunction with the training database 242. The training functionality may provide the user 104, for example, with a guided tour of a facility, alert the user 104 to safety concerns, and overlay additional computer information on the actual environment. For example, an overlay may show the contents of a pipe or tank, the flow of liquid, reveal the invisible to show to the user 104 what is either not built or cannot be seen. Thus, the training functionality may increase proficiency of the user 104, and reduce training time.

The maintenance control module 212 may implement maintenance functionality for the user 104, for example, to use the context based AR glasses 114 to look at a piece of equipment or machinery, have that equipment recognized using computer vision, and to provide the user 104 with a checklist of activities to perform a particular maintenance activity and/or to augment the user's view with computer drawings and designs that show how to perform a particular maintenance activity. The maintenance functionality may further allow the user 104 to advance tasks, for example, by using their voice (e.g., by saying next task), to order parts for a particular step using their voice, to allow remote users to draw on what the user 104 is seeing, and to record the entire maintenance process for further analysis and review either by computer analytics or manually. The maintenance functionality may thus provide for maintenance history and checklist capability, and step-by-step repair guidance to the user 104. These aspects may provide for reduction in repair time, increase in repair quality, and may further facilitate ease of recording of maintenance activity.

The safety control module 214 may implement safety functionality for the user 104, for example, to geographically track the user 104 via the context based AR glasses 114, and alert the user 104 when they have moved into a dangerous location or an unauthorized area. The safety control module 214 may also alert the user 104 when an equipment they are looking at is safely shut down, or whether it is still live and dangerous. In addition, the safety control module 214 may provide audio and/or visual alerts for a particular piece of equipment, and track the user's eye movement to see if the user is focusing on the right tasks. Tracking of the location of the user 104 and/or the personnel 106 may be performed through the use of a real time location system. Alternatively or additionally, tracking of the location of the user 104 may be performed through the use of a GPS if the user 104 and/or the personnel 106 are outside of an enclosed building and have access to the cell tower 108, and/or the satellite 112. The safety functionality provided by the safety control module 214 may include, for example, go/no-go zone identification, safety alerts, and/or lock-out/tag-out operations. The safety functionality may provide for decrease in safety-violation incidents, and increase in awareness of the user 104, and/or intervention by the personnel 106.

Figure 3A:
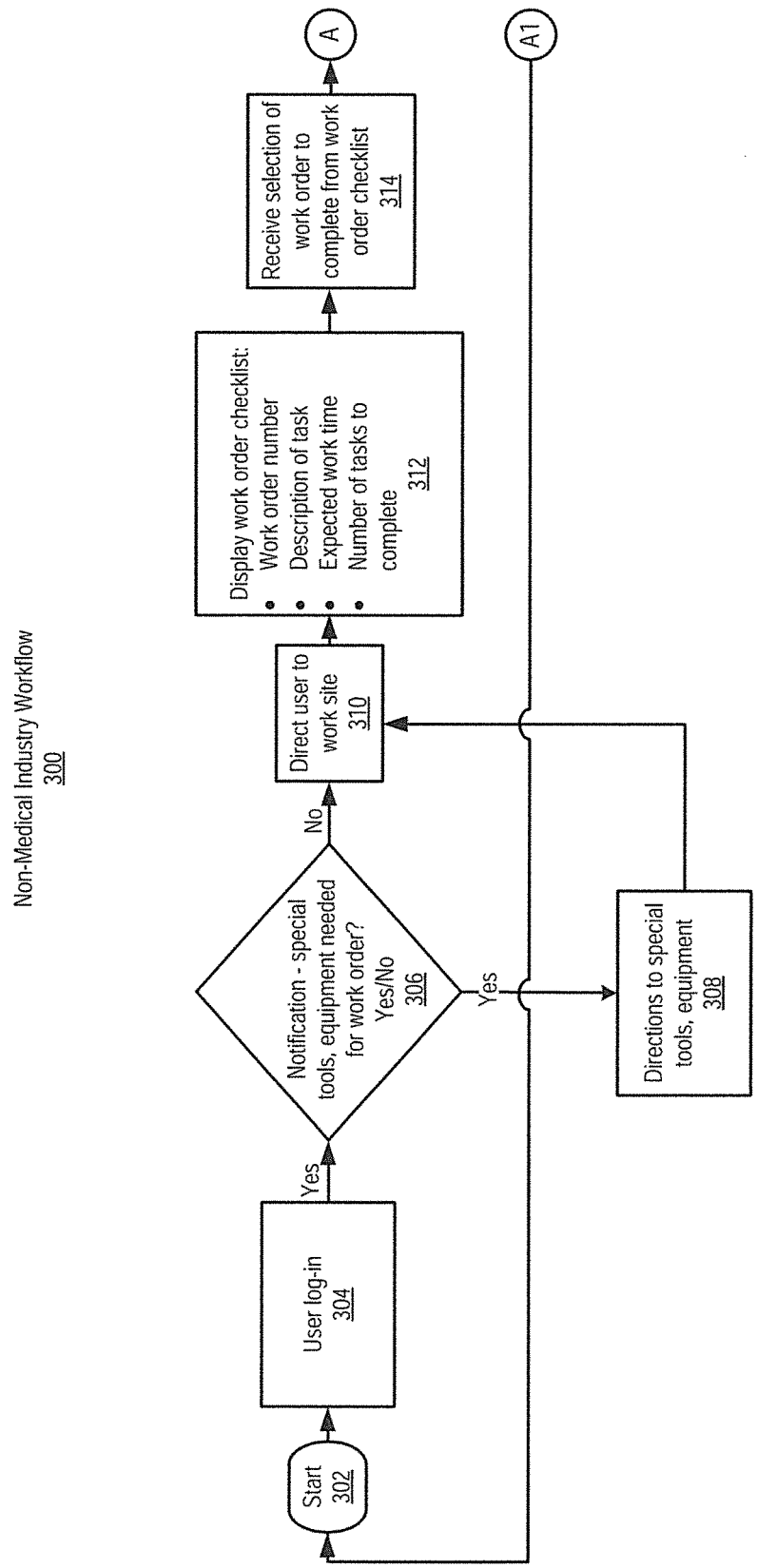
FIGS. 3A-3C illustrate a flowchart of a non-medical industry workflow for context based AR, according to an example of the present disclosure.
Figure 3B:
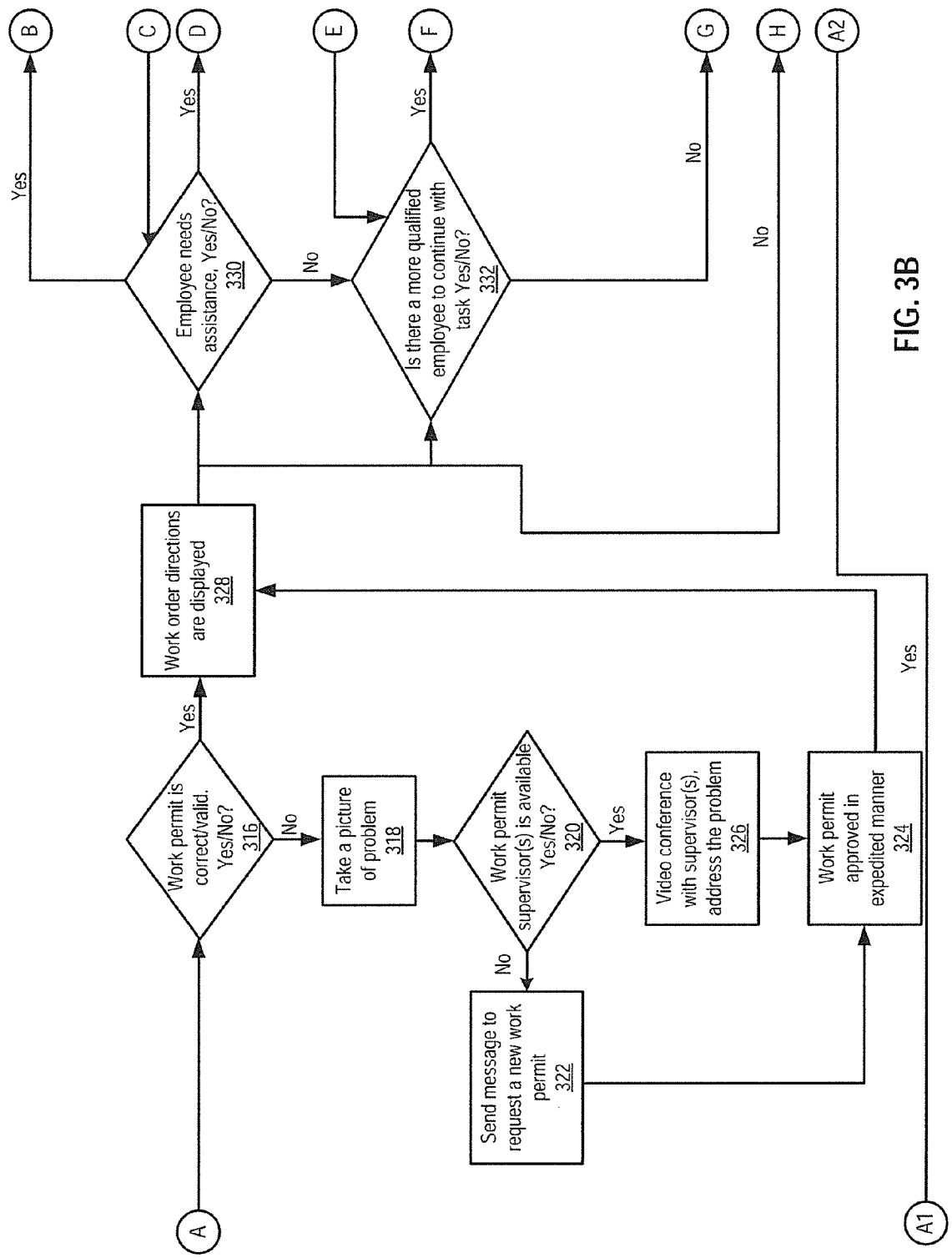
Figure 3C:
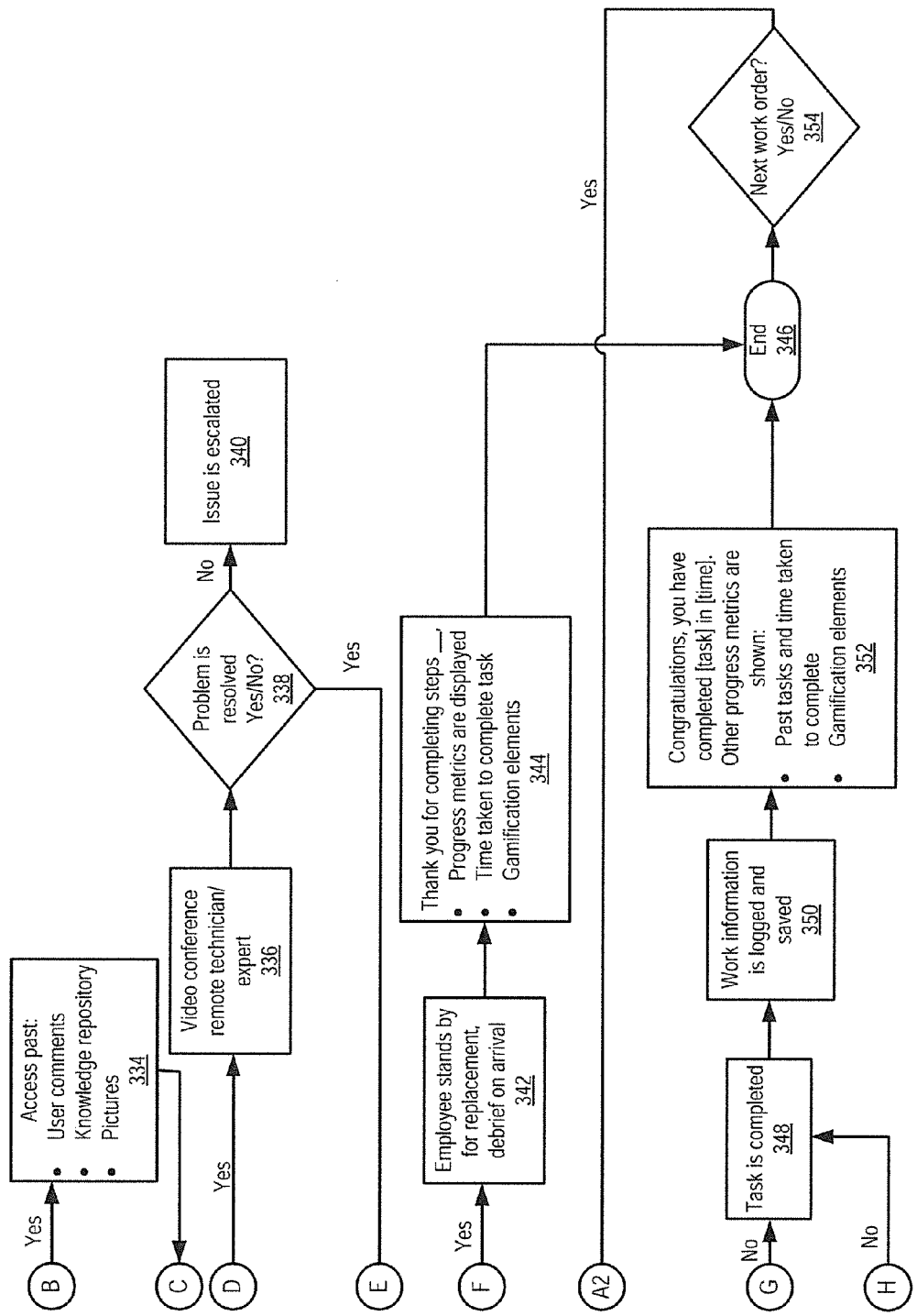

FIGS. 3A-3C illustrate a flowchart of a non-medical industry workflow 300 for context based AR, according to an example of the present disclosure.

Referring to FIG. 3A, at block 302, the user 104 may begin a workflow. For example, the user 104 such as, for example, a field technician, may begin a workflow, for example, in the field of oil and gas, and other such fields, where field workers and other personnel are required to wear safety glasses when in any high risk location.

At block 304, the user 104 may use the context based AR glasses 114 with the context based AR system 102 to log-in. The log-in may be performed by the user log-in module 216, for example, based on voice recognition, a retina eye scan, and/or other techniques for identifying the user 104. As described in further detail with reference to the no current work orders logic 400 of FIG. 4, based on the log-in by the user 104, the no current work orders logic module 222 may generally scan work that has been assigned to the user 104, and determine work that meets the user's skills and availability.

As described in further detail with reference to the no current work orders logic 400 of FIG. 4, based on the assignment of a work order to the user 104, at block 306, a determination may be made as to whether the user 104 is to be notified of any special tools or equipment that is needed for the work order.

Based on a determination at block 306 that special tools or equipment is needed for the work order, at block 308, the user 104 may be provided directions to the special tools or equipment that is needed for the work order.

Based on a determination at block 306 that no special tools or equipment is needed for the work order, or following block 308, the user 104 may be directed to the appropriate work site at block 310.

At block 312, a work order checklist may be displayed. The work order checklist may include, for example, a work order number, a description of a task to be performed for the work order, an expected work time for the task to be performed for the work order, and a number of tasks to complete for the work order. The work order checklist may be displayed to the user 104 by the context based AR glasses 114 while the user 104 is in route to the work site. The work order checklist may include a plurality of work orders and related information.

At block 314, the workflow control module 122 may receive, from the user 104, selection of a work order to complete from the work order checklist. For example, the work order may be selected by a voice command from the user 104 by the context based AR glasses 114. Alternatively or additionally, the work order may be selected by a touch, gaze, and/or head position of the user 104 relative to the context based AR glasses 114 upon arrival at the work site. Alternatively or additionally, the work order may start automatically (i.e., without human intervention) upon the user's arrival at the work site.

Referring to FIG. 3B, at block 316, based on the work order determined at block 314, the work permit determination module 220 may ascertain an appropriate work permit for the user 104 by first determining if a work permit is correct (i.e., valid). The condition at block 316 may be checked after each direction is completed through the work order.

Based on a determination at block 316 that the work permit is not correct, at block 318, the context based AR glasses 114 may be used by the user 104 to take a picture of the problem with the work permit. For example, the context based AR glasses 114 may be used to take a picture of the problem with the work permit, and any information (e.g., the picture and/or notes) related to the problem with the work permit may be stored, for example, in the safety database 246.

At block 320, the work permit determination module 220 may determine if a work permit supervisor is available to address the problem with the work permit.

Based on a determination at block 320 that the work permit supervisor is not available to address the problem with the work permit, at block 322, a message may be sent to a work permit authority to request a new work permit.

At block 324, following block 322, the new work permit may be approved in an expedited manner.

Based on a determination at block 320 that the work permit supervisor is available, at block 326, a video conference may be initiated with the supervisor to address the problem with the work permit of block 318. For example, the video analytics and computer vision module 204 may be used to initiate a video conference with the supervisor to address the problem with the work permit of block 318.

Further, at block 324, once the problem at block 318 is addressed, the work permit may be approved in an expedited manner. As described in further detail with reference to FIG. 5, based on the video conference initiated at block 326, the request work permit module 224 may implement the request work permit logic 500.

Based on a determination at block 316 that the work permit is correct, at block 328, work order directions may be displayed using the context based AR glasses 114. For example, work order directions may be displayed as a step-by-step process for the user 104. Each direction may be displayed with an accompanying graphic. The work order directions may be displayed to take up a partial or a whole view of the context based AR glasses 114.

At block 330, a determination may be made as to whether the user 104 (e.g., an employee) needs assistance for the work order.

Based on a determination at block 330 that the user 104 does not need assistance, at block 332, a determination may be made as to whether there is a more qualified user 104 (e.g., a more qualified employee) to continue with the task related to the work order. In this regard, the collaboration integration module 202 may review available employees, and match employee experience and skill level with available/ongoing tasks related to the work order.

Referring to FIG. 3C, based on a determination at block 330 that the user 104 needs assistance, at block 334, the collaboration integration module 202 may access information from past user comments, knowledge repositories, and pictures. For example, the collaboration integration module 202 may access the training database 242, maintenance database 244, safety database 246, asset database 248, GIS database 250, and/or user database 252. Further to the determination at block 334, processing may revert back to block 330.

Further, based on a determination at block 330 that the user 104 needs assistance, at block 336, the video analytics and computer vision module 204 may initiate a video conference with the personnel 106 (e.g., a remote technician/expert). As described in further detail with reference to FIG. 6, the video conference initiated at block 336 may initiate the user assistance logic 600 of FIG. 6.

At block 338, the collaboration integration module 202 may determine whether any problem at block 330 is resolved.

Based on a determination at block 338 that the problem at block 330 is not resolved, at block 340, the issue may be escalated. Otherwise, based on a determination at block 338 that the problem at block 330 is resolved, processing may revert back to block 332.

Based on a determination at block 332 that there is a more qualified user 104 (e.g., a more qualified employee) to continue with the task related to the work order, at block 342, the initial user 104 may stand by for replacement. Further, the initial user 104 may be debriefed on arrival of the more qualified user 104.

At block 344, for the initial user 104, the initial user 104 may be advised of the completed steps of the task related to the work order. For example, progress metrics, time taken to complete the task, and/or gamification elements may be displayed using the context based AR glasses 114 for the initial user 104 and the new user 104.

At block 346, the non-medical industry workflow 300 for context based AR may be completed for the work order selected at block 314.

Based on a determination at block 332 that a more qualified user 104 (e.g., a more qualified employee) is not available to continue with the task related to the work order, at block 348, the task may be completed by the initial user 104. Block 348 may also be initiated after block 328 where work order directions may be displayed using the context based AR glasses 114.

At block 350, work information related to the task may be logged and saved, for example, in the user database 252. For example, the status of the task may be changed from active to complete.

At block 352, the user 104 may be provided with information related to the completed task related to the work order. For example, the user 104 may be provided with the time taken to complete the task. Other progress metrics may include, for example, past tasks and time taken to complete the past tasks, gamification elements, etc.

At block 354, a next work order may be determined for the non-medical industry workflow 300. Based on a determination at block 354 of a next work order, the non-medical industry workflow 300 may revert to block 302.

Figure 4:
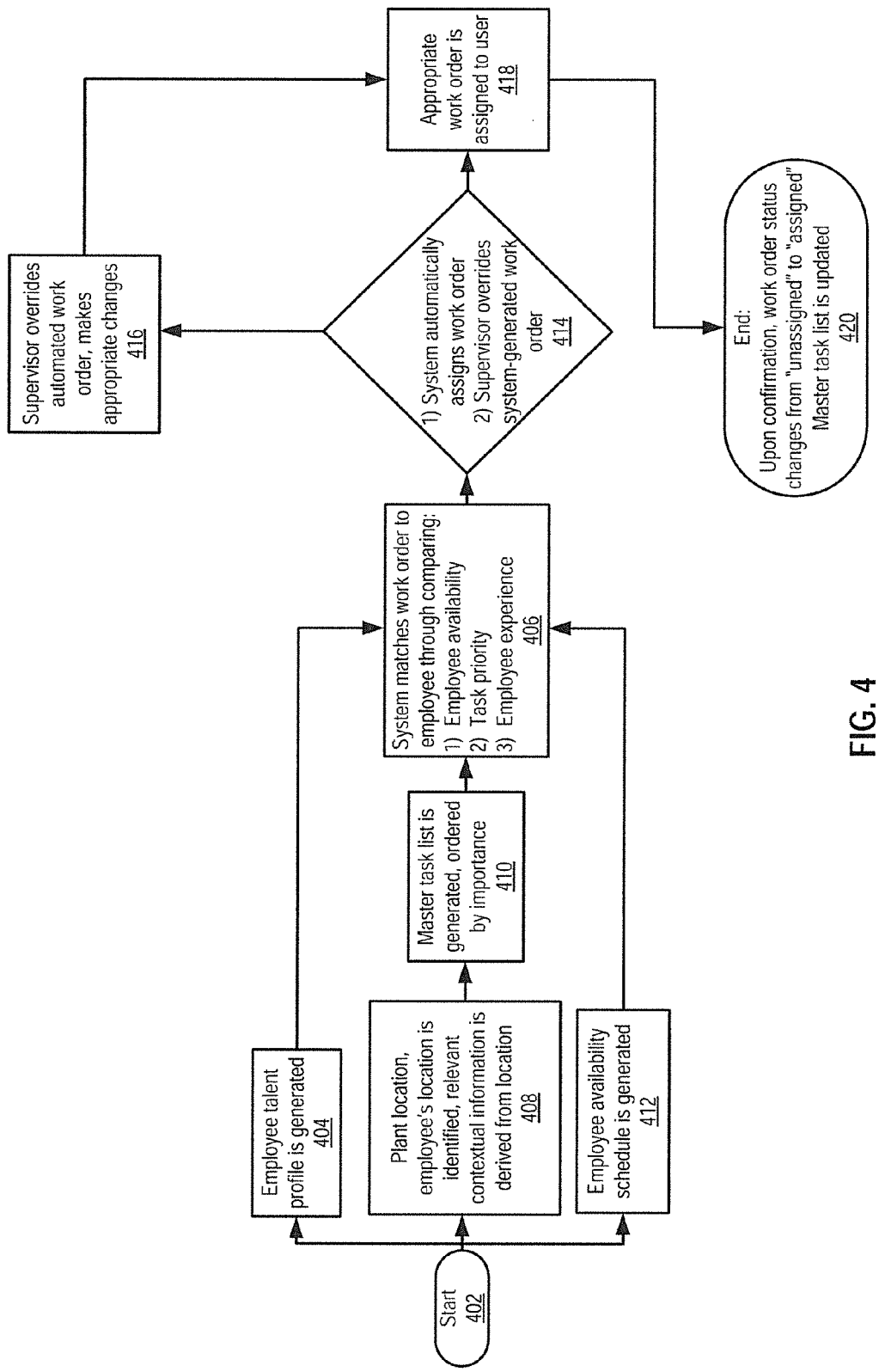
FIG. 4 illustrates a flowchart of a no current work orders logic for the workflow of FIGS. 3A-3C, according to an example of the present disclosure.

Referring to FIG. 4, for the no current work orders logic 400 of FIG. 4, based on the log-in by the user 104 at block 304 of FIG. 3, the no current work orders logic module 222 may generally scan work that has been assigned to the user 104, and determine work that meets the user's skills and availability.

At block 402, the no current work orders logic 400 may start. At block 402, the personnel 106, such as, for example, a back office supervisor, may access various information related to the user 104 and/or tasks. For example, the personnel 106 may ascertain progress of the user 104 (or other employees) on a task. The personnel 106 may also ascertain, for example, necessary tasks that are to be implemented, idle time for tools/processes, reasons for any downtime, parts that are requested, and/or plant-wide open tasks.

At block 404, the talent profile of the user 104 (e.g., an employee) may be generated. The talent profile may include, for example, skills, certifications, past projects, past performance, years of experience, language, etc., related to the user 104.

At block 406, the no current work orders logic module 222 may match work order to the user 104 by comparing, for example, user availability, task priority, and/or user experience.

At block 408, the no current work orders logic module 222 may determine location of the worksite (e.g., plant) where the task is to be performed.

Further, the no current work orders logic module 222 may determine the location of the user 104 by using the context based AR glasses 114, and derive other relevant contextual information from the location.

At block 410, a master task list may be generated, and ordered by importance.

At block 412, the no current work orders logic module 222 may generate an availability schedule for the user 104. The availability schedule may account for any possible tasks the user 104 is assigned throughout the day. For example, an eight hour task will not be assigned to a user 104 who has four hours available.

At block 414, based on the matching of the work order to the user 104 at block 406, the no current work orders logic module 222 may assign a work order to the user 104. Alternatively, the personnel 106 (e.g., a supervisor) may override the determination by the no current work orders logic module 222 to assign a different work order.

At block 416, the personnel 106 (e.g., a supervisor) may override the work order assigned by the no current work orders logic module 222 and enter appropriate changes to the work order. For example, if the personnel 106 are clear about deadlines, long-term and/or short-term objectives, and/or overall project progress, the personnel 106 may make informed decisions to make appropriate changes.

At block 418, an appropriate work order may be assigned to the user 104.

At block 420, upon confirmation, the work order status may be changed from unassigned to assigned, and the master task list may be updated.

Figure 5:
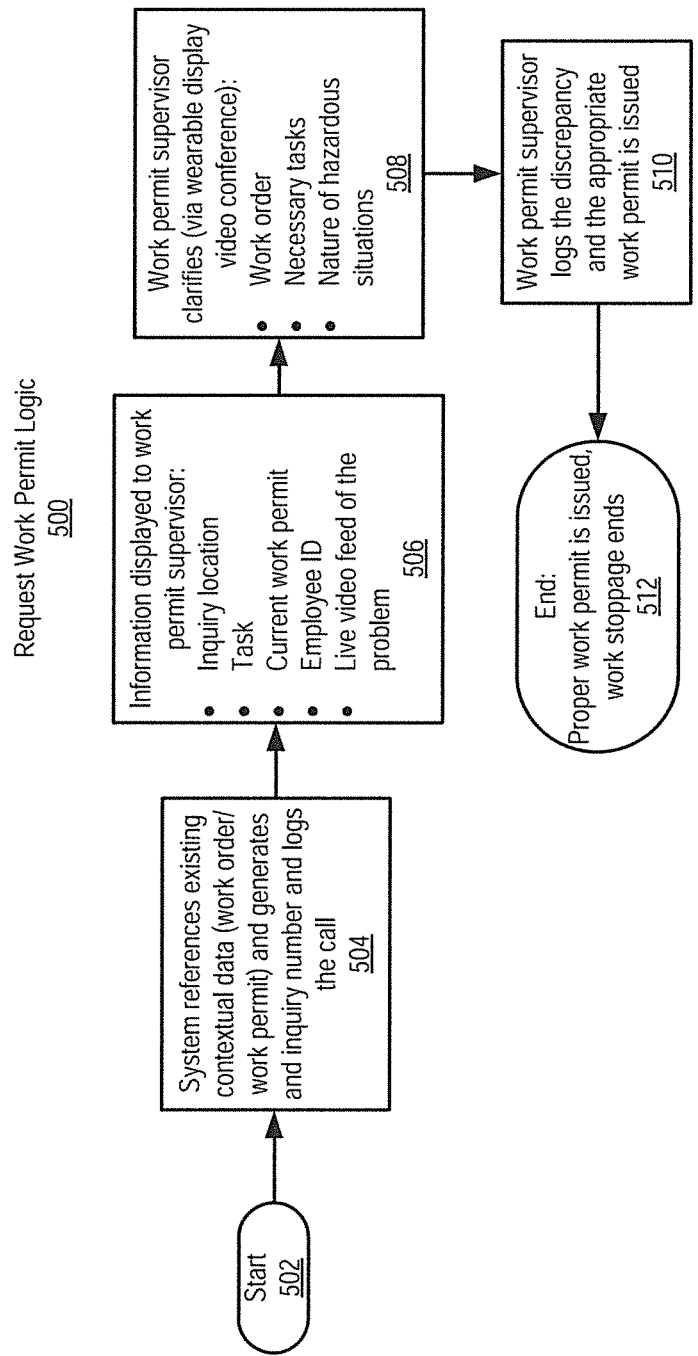
FIG. 5 illustrates a flowchart of a request work permit logic for the workflow of FIGS. 3A-3C, according to an example of the present disclosure.

Referring to FIG. 5, for the request work permit logic 500 of FIG. 5, based on the video conference initiated at block 326 of FIG. 3, the request work permit module 224 may implement the request work permit logic 500.

At block 502, the request work permit logic 500 may start.

At block 504, the request work permit module 224 may reference existing contextual date (e.g., work order, work permit, etc.), generate an inquiry number, and log a call associated with the work permit request.

At block 506, the information obtained at block 504 may be displayed to the personnel 106 (e.g., a work permit supervisor). For example, the information may be displayed via a set of the context based AR glasses 114 to the personnel 106. The information may include, for example, an inquiry location, task information, current work permit, an identification (ID) for the user 104, and/or a live video feed of any problem associated with the work permit.

At block 508, the personnel 106 (e.g., a work permit supervisor) may clarify, via the context based AR glasses 114, information related to the work order, necessary tasks, and/or a nature of hazardous situations.

At block 510, the personnel 106 (e.g., a work permit supervisor) may log any discrepancy, and the appropriate work permit may be issued. The information at block 510 may be tagged in the task related to the work permit as that the on-site user 104 had an issue with, and may be stored in the user database 252. The information at block 510 may be reviewed at a later time. The information may be used to ensure that work permits are issued for appropriate work orders. Further, the information may also be made accessible to other users to mitigate any confusion related to the work permit.

At block 512, the appropriate work permit may be issued, and any work stoppage related to the work permit may be terminated.

Figure 6:
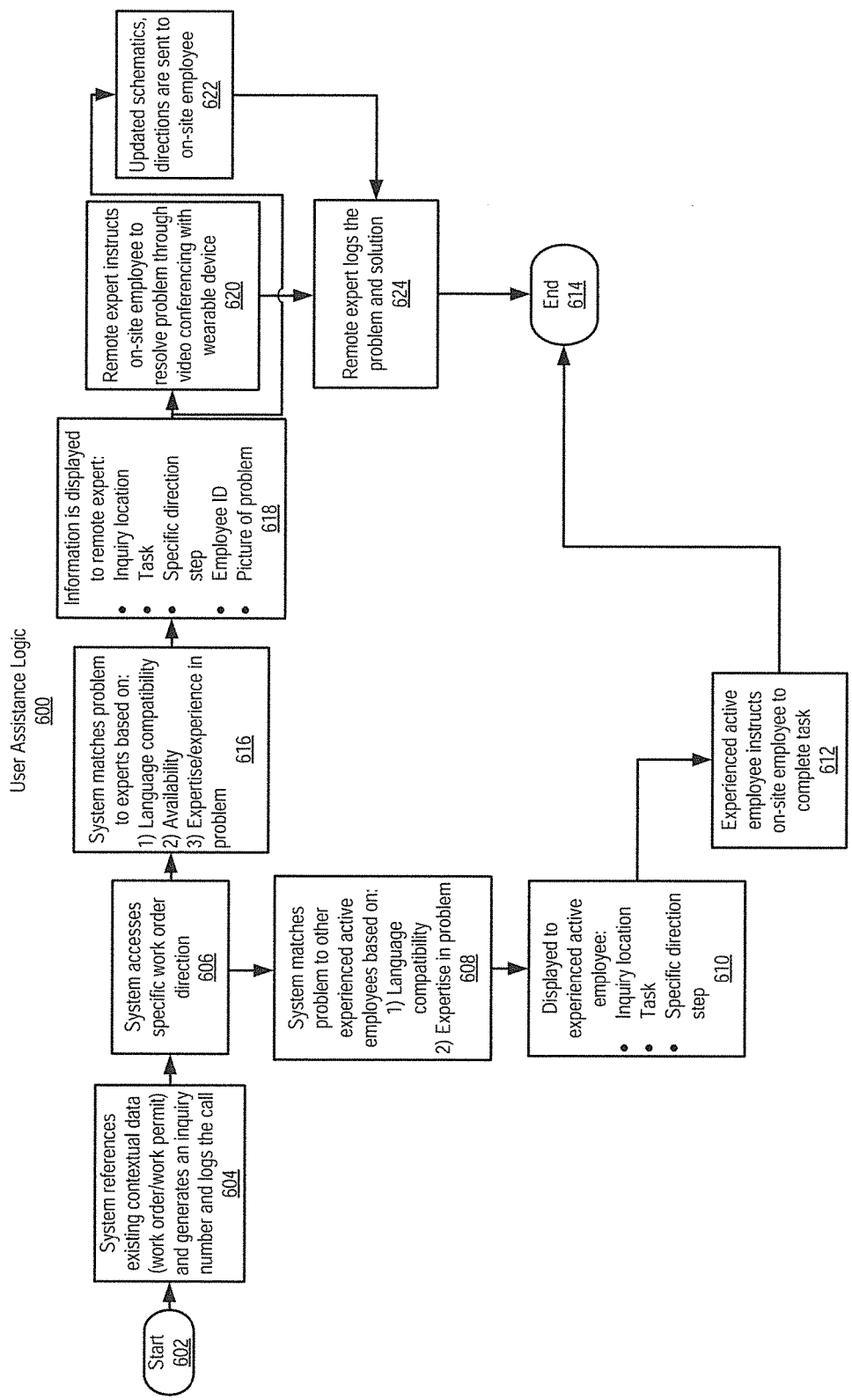
FIG. 6 illustrates a flowchart of a user assistance logic for the workflow of FIGS. 3A-3C, according to an example of the present disclosure.

Referring to FIG. 6, for the user assistance logic 600 of FIG. 6, based on the video conference initiated at block 336 of FIG. 3, the user assistance module 226 may implement the user assistance logic 600.

At block 602, the user assistance logic 600 may start.

At block 604, the user assistance module 226 may reference existing contextual data (e.g., work order/work permit). Further, the user assistance module 226 may generate an inquiry number and log a call associated with the user assistance.

At block 606, the user assistance module 226 may access specific work order direction.

At block 608, the user assistance module 226 may match the problem that the initial user 104 needs assistance with to other experienced active users 104 based, for example, on language compatibility and/or expertise for addressing a problem. For example, the user assistance module 226 may provide a peer to peer assistance option if there are no experts available to address the problem.

At block 610, the context based AR glasses 114 may be used to display, for example, an inquiry location, task information, and a specific direction step to an experienced active user 104.

At block 612, the experienced active user 104 may instruct the on-site user 104 to complete the task.

At block 614, the user assistance logic 400 may terminate.

At block 616, the user assistance module 226 may match the problem to the personnel 106 (e.g., experts), based, for example, on language compatibility, availability, and/or expertise and experience for addressing the problem.

At block 618, the context based AR glasses 114 may be used to display, for example, information to the remote personnel 106 (e.g., remote expert). The information may include, for example, inquiry location, task details, specific direction step, user ID, and/or a picture of the problem.

At block 620, the remote personnel 106 (e.g., remote experts) may instruct the on-site user 104 (e.g., on-site employee) to resolve the problem, for example, via video conferencing using the context based AR glasses 114. The video conferencing may be implemented by the video analytics and computer vision module 204 and the audio search module 206.

At block 622, updated schematics and/or directions related to the problem may be sent to the on-site user 104 (e.g., on-site employee).

At block 624, the remote personnel 106 (e.g., remote experts) may log the problem and solution. For example, the problem and solution may be tagged to the specific direction that the on-site user 104 had an issue with and may be stored in the user database 252. The problem and solution may be reviewed at a later time, and used to update the directions, or inform/clarify on-site users of any vague directions. Further, this information may be made accessible to on-site users to mitigate confusion.

Figure 7:
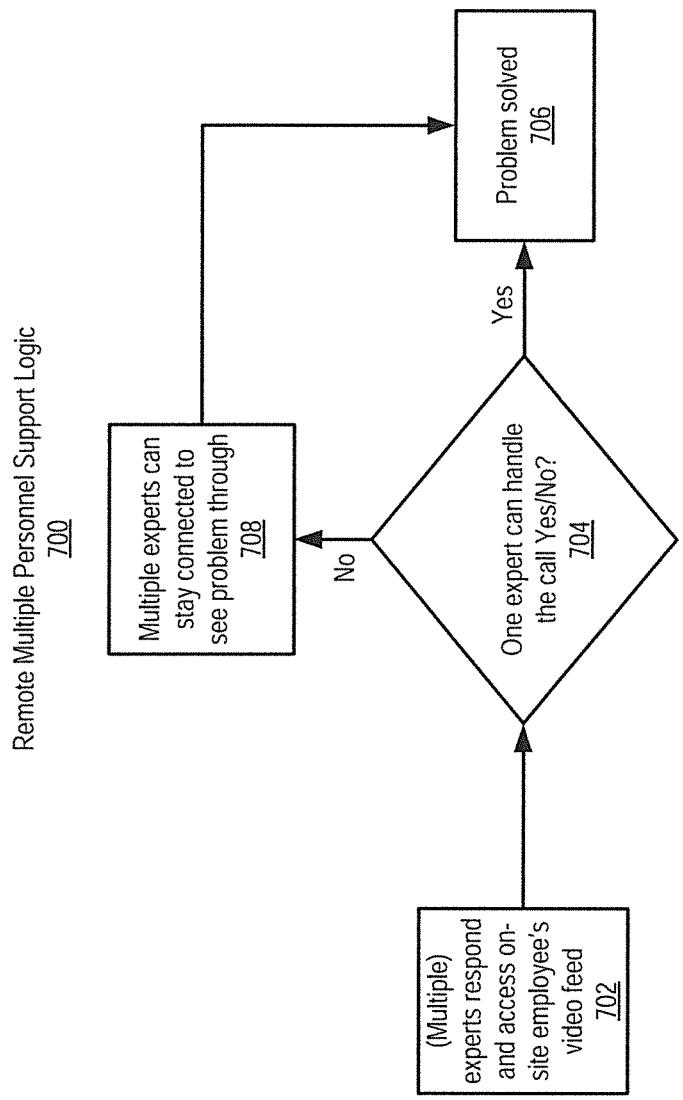
FIG. 7 illustrates a flowchart of a remote multiple personnel support logic for the workflow of FIGS. 3A-3C, according to an example of the present disclosure.

Referring to FIG. 7, for the remote multiple personnel support logic 700 of FIG. 7, based on the video conference initiated at block 336 of FIG. 3, for multiple remote personnel, the remote multiple personnel support module 228 may implement the remote multiple personnel support logic 700.

At block 702, multiple remote personnel 106 (e.g., multiple remote experts) may respond and access the user's (e.g., the on-site employee) video feed using, for example, the context based AR glasses 114 assigned to each of the multiple remote personnel 106.

At block 704, a determination may be made as to whether one of the remote personnel 106 can handle the call from the user 104.

Based on a determination at block 704 that one of the remote personnel 106 can handle the call from the user 104, at block 706, the problem may be solved by the appropriate remote personnel 106.

Based on a determination at block 704 that multiple remote personnel 106 are needed to handle the call from the user 104, at block 708, multiple remote personnel 106 may stay connected to the user 104 to resolve the problem.

Figure 8:
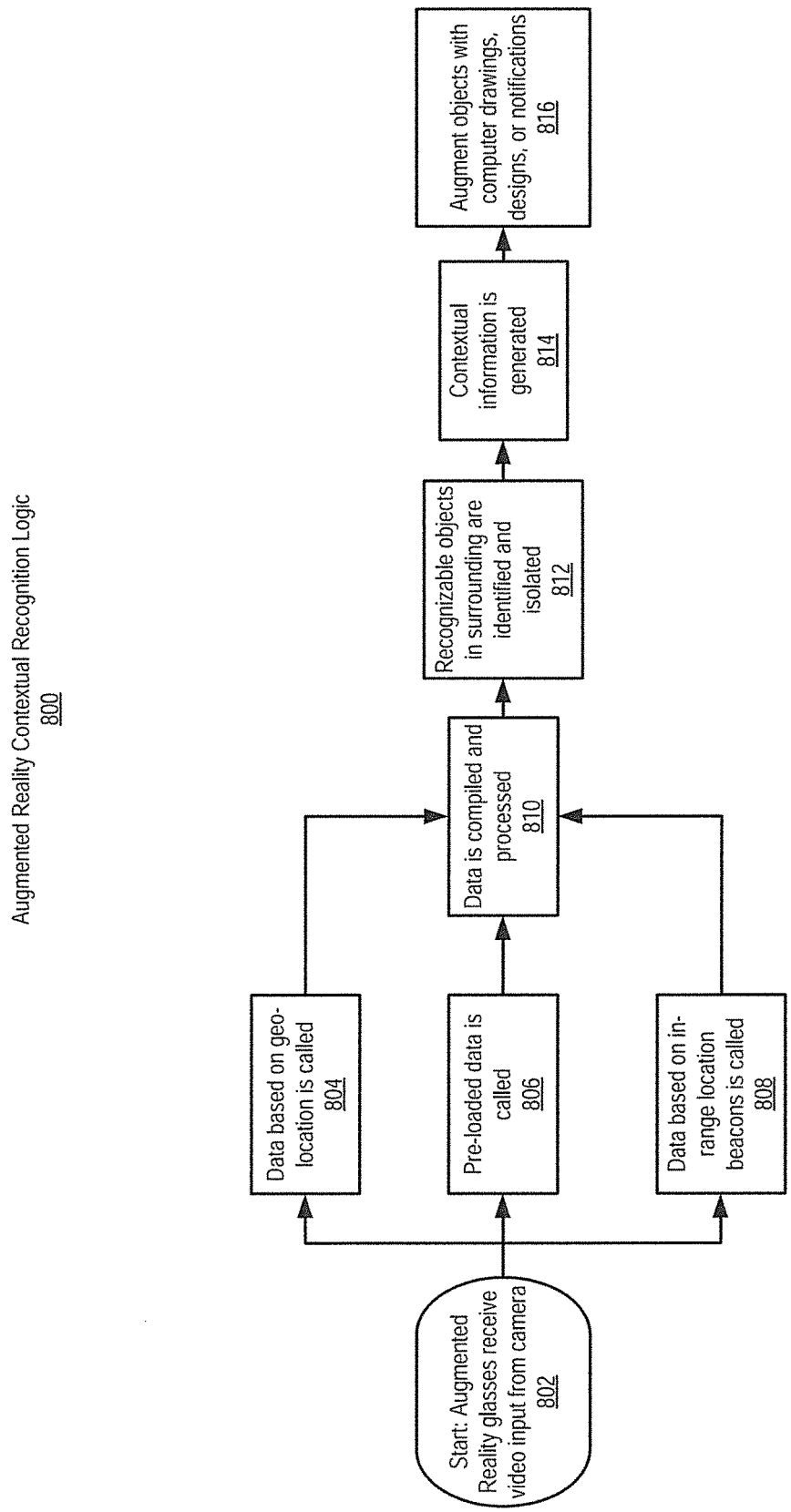
FIG. 8 illustrates a flowchart of an AR contextual recognition logic for the workflow of FIGS. 3A-3C, according to an example of the present disclosure.

Referring to FIG. 8, for the AR contextual recognition logic 800 of FIG. 8, the AR contextual recognition module 230 may implement the AR contextual recognition logic 800. The AR contextual recognition logic 800 may be applied to all processes related to the non-medical industry workflow 300 and the medical industry workflows 1000, 1100, 1200, and 1300.

At block 802, the context based AR glasses 114 may receive video input from the camera associated therewith.

At block 804, the AR contextual recognition module 230 may call data based on geographic location. For example, the context based AR glasses 114 may be tracked geographically, and alert the user 104 when the user has moved into a prohibited or otherwise dangerous location.

At block 806, the AR contextual recognition module 230 may call pre-loaded data. The pre-loaded data may include, for example, computer-aided design (CAD) renderings, three-dimensional (3D) objects, etc.

At block 808, the AR contextual recognition module 230 may call data based on in-range location beacons. For example, location beacons with preloaded notifications may be placed around specific areas that require attention.

At block 810, the data ascertained at blocks 804, 806, and 808 may be compiled and processed.

At block 812, recognizable objects in the environment zone 116 (e.g., the surrounding) may be identified and isolated.

At block 814, contextual information may be generated. For example, the contextual information may include information based on equipment state, ongoing tool processes, and/or hazardous materials.

At block 816, objects may be augmented, for example, with computer drawings, designs, and/or notifications.

Figure 9:
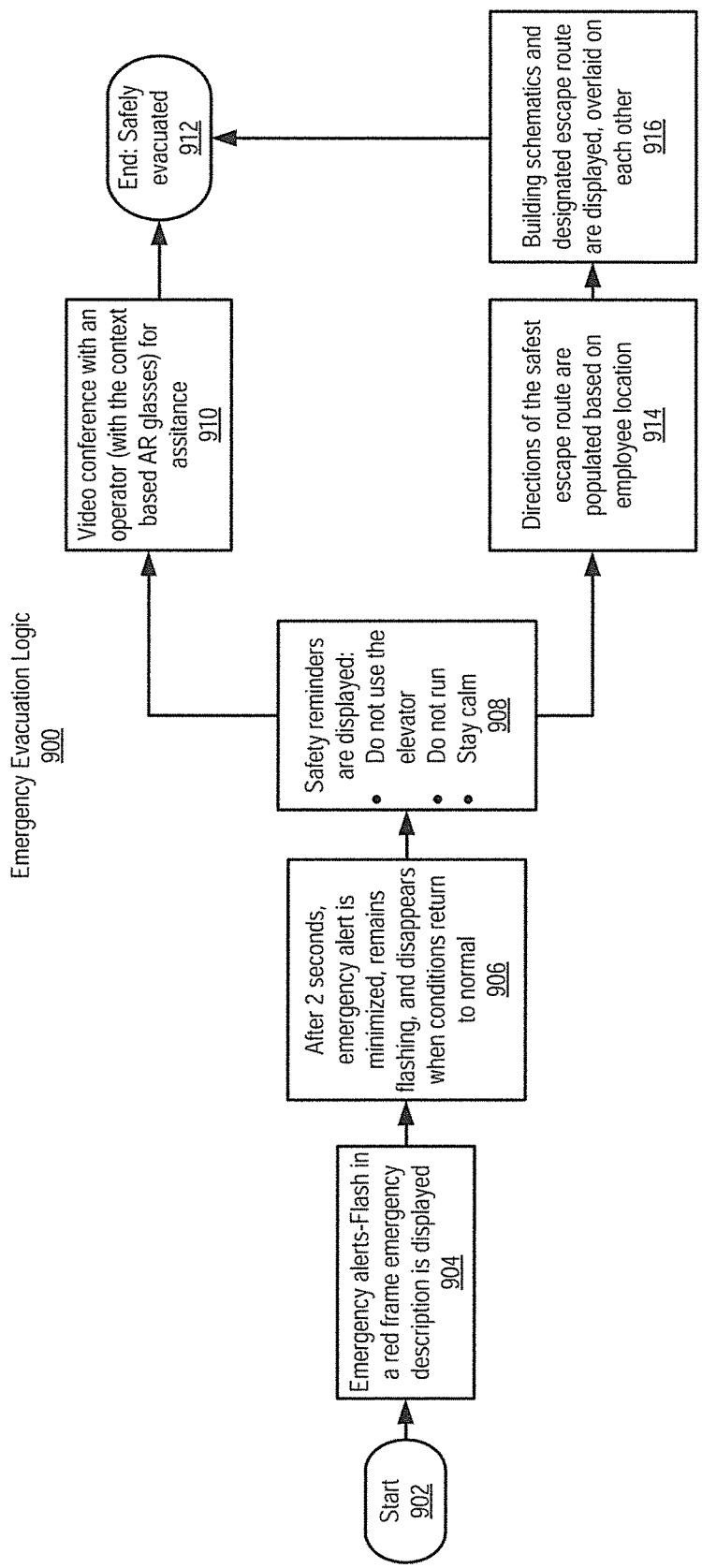
FIG. 9 illustrates a flowchart of an emergency evacuation logic for the workflow of FIGS. 3A-3C, according to an example of the present disclosure.

Referring to FIG. 9, for the emergency evacuation logic 900 of FIG. 9, the emergency evacuation control module 232 may implement the emergency evacuation logic 900. The emergency evacuation logic 900 may be applied to all processes related to the non-medical industry workflow 300 and the medical industry workflows 1000, 1100, 1200, and 1300.

At block 902, the emergency evacuation logic 900 may start.

At block 904, the emergency evacuation control module 232 may provide for emergency alerts. For example, the emergency evacuation control module 232 may provide for flashing alerts, for example, in a red frame emergency description displayed using the context based AR glasses 114.

At block 906, after a predetermined time duration (e.g., 2 seconds), the emergency alert may be minimized. Further, the emergency alert may remain flashing, and disappear when conditions related to the emergency alert return to normal.

At block 908, safety reminders may be displayed. For example, the safety reminders may include reminders, such as, for example, not to use the elevator, not to run, stay calm, etc.

At block 910, the emergency evacuation control module 232 may provide for the initiation of a video conference with the personnel 106 (e.g., an operator with the context based AR glasses 114) for assisting the user 104.

At block 912, based on the assistance provided by the personnel 106, the emergency evacuation logic 900 may end upon the safe evacuation of the user 104.

At block 914, directions of the safest escape route may be populated based on the location of the user 104. The directions may be displayed to the user 104 at the context based AR glasses 114 worn by the user 104. The emergency evacuation control module 232 may update the information and directions in real-time.

At block 916, the user 104 may also be provided with any building schematics and designated escape routes at the context based AR glasses 114 worn by the user 104. Such schematics and designated escape routes may be overlaid on each other.

Referring to FIG. 10, for the trauma EMT response logic 1000 of FIG. 10, the trauma EMT response module 234 may implement the trauma EMT response logic 1000.

At block 1002, the trauma EMT response logic 1000 may start.

At block 1004, the user 104 (e.g., an EMT) of the context based AR glasses 114 may be provided with a data view that includes, for example, a location of the incident, an injury background of a patient that is being treated, a patient status, patient vitals, patient heart rate, patient name, patient weight and height, patient blood type, patient estimated time of arrival to a hospital, and treatment rendered at the location of the incident. The data view may be provided at the context based AR glasses 114 worn by the user 104. In this regard, the user 104 may use the context based AR glasses 114 with voice activated commands to send information to the personnel 106 (e.g., physicians) at a hospital. The data related to the data view provided to the user 104 may be added to the data view as the data is compiled and becomes available to/from the user 104, who may be a first responder.

At block 1006, the user 104 may alert the hospital of the patient's arrival.

Figure 11:
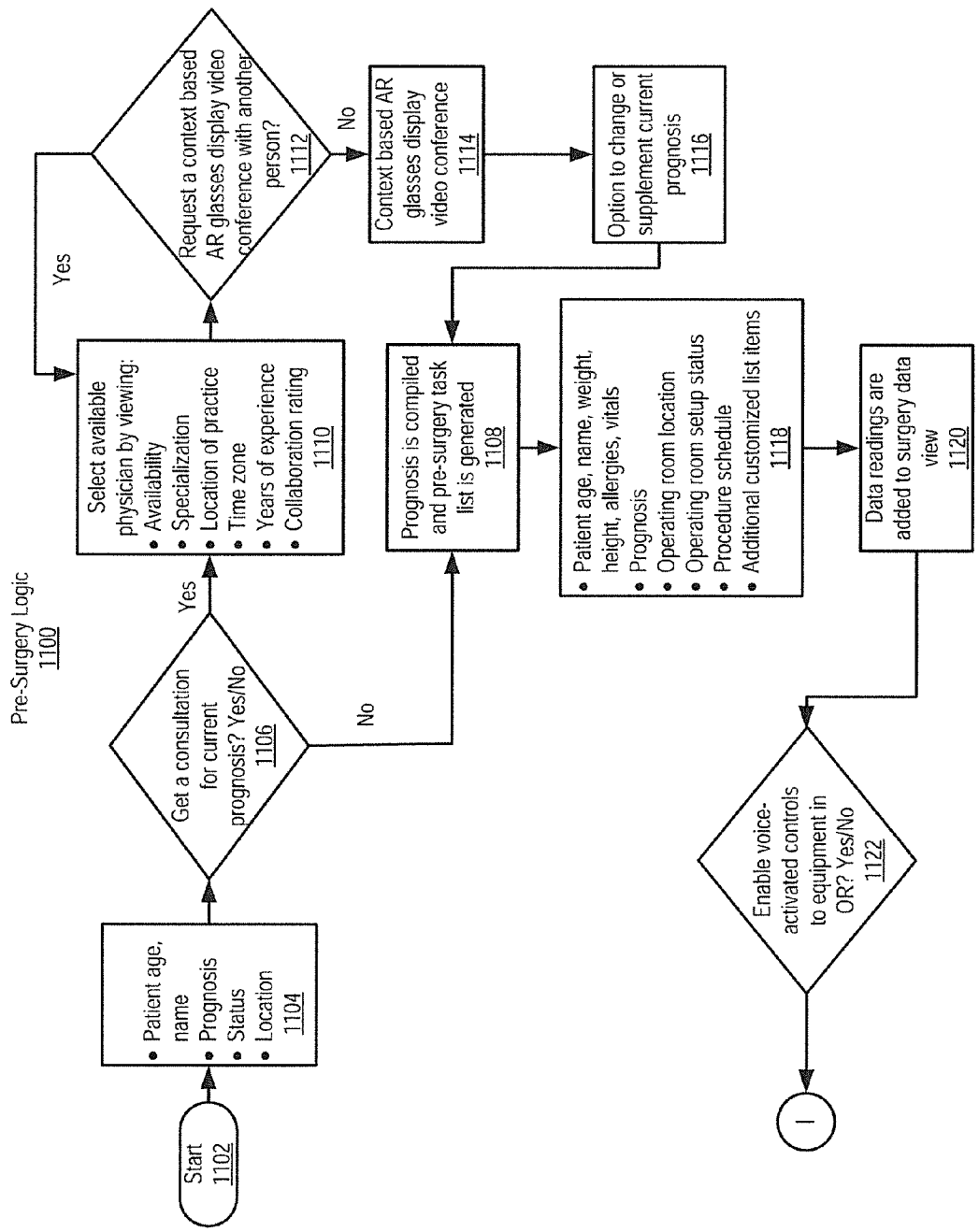
FIG. 11 illustrates a flowchart of a pre-surgery logic, according to an example of the present disclosure.

Referring to FIG. 11, for the pre-surgery control logic 1100 of FIG. 11, the pre-surgery control module 236 may implement the pre-surgery control logic 1100.

At block 1102, the pre-surgery control logic 1100 may start.

At block 1104, a user 104 (e.g., a physician or another medical staff member receiving the patient) may receive and/or enter vital information related to the patient, such as, for example, the patient's age, prognosis, status, and/or location. The user 104 for the pre-surgery control logic 1100 may receive and/or enter the information at block 1104 at the context based AR glasses 114 worn by the user 104. The information received and/or entered may be based on the information ascertained during implementation of the trauma EMT response logic 1000 and the pre-surgery logic 1100.

At block 1106, the user 104 receiving the patient may determine whether to obtain a consultation for the current prognosis determined at block 1104. For example, the user 104 receiving the patient may determine whether to obtain a consultation for the current prognosis from a specialist at another hospital.

Based on a determination at block 1106 that a consultation for the current prognosis determined at block 1104 is not needed, at block 1108, the prognosis obtained at 1104 may be compiled with other information obtained, for example, at block 1116 described below. Further a pre-surgery task list may be generated. Determination of a prognosis may be based on patient records and/or assessments of the users 104 that may include first responders and/or physicians.

Based on a determination at block 1106 that a consultation for the current prognosis determined at block 1104 is needed, at block 1110, the pre-surgery control module 236 may provide a view of available physicians, for example, by availability, specialization, location of practice, time zone, years of experience, and/or collaboration rating. The view may be provided at the context based AR glasses 114 worn by the user 104.

At block 1112, a context based AR glasses 114 video conference may be requested with one or more personnel 106 (e.g., other physicians).

Based on a determination at block 1112 that a context based AR glasses 114 video conference is not requested with another person, at block 1114, a context based AR glasses 114 video conference may initiate with the original personnel 106. The user 104 may initiate the video conference and/or the personnel 106 may use the context based AR glasses 114 to implement the video conference at block 1114. Alternatively, based on a determination at block 1112 that a context based AR glasses 114 video conference is requested with another person, processing may revert to block 1110.

At block 1116, the current prognosis may be changed or supplemented based on the video conference at block 1114.

At block 1118, various aspects related to the patient may be finalized for the pre-surgery logic 1100. For example, aspects related to patient age, patient name, patient weight, patient height, patient allergies, and patient vitals, the prognosis, operating room location, operating room setup status, procedure schedule, and/or additional customized list items may be finalized.

At block 1120, various data readings may be added to the surgery data view for the user 104 (e.g., a physician) that is to perform the surgery. The data readings added to the surgery data view may be specified and/or chosen by the user 104 as needed for performing the surgery. Based on context, the display for the context based AR glasses 114 may be divided into quadrants with, for example, the four most crucial data views shown. Alternatively or additionally, data views may be set to scroll through pertinent data.

At block 1122, a determination may be made as to whether to enable voice-activated controls to equipment needed for the surgery.

Figure 12A:
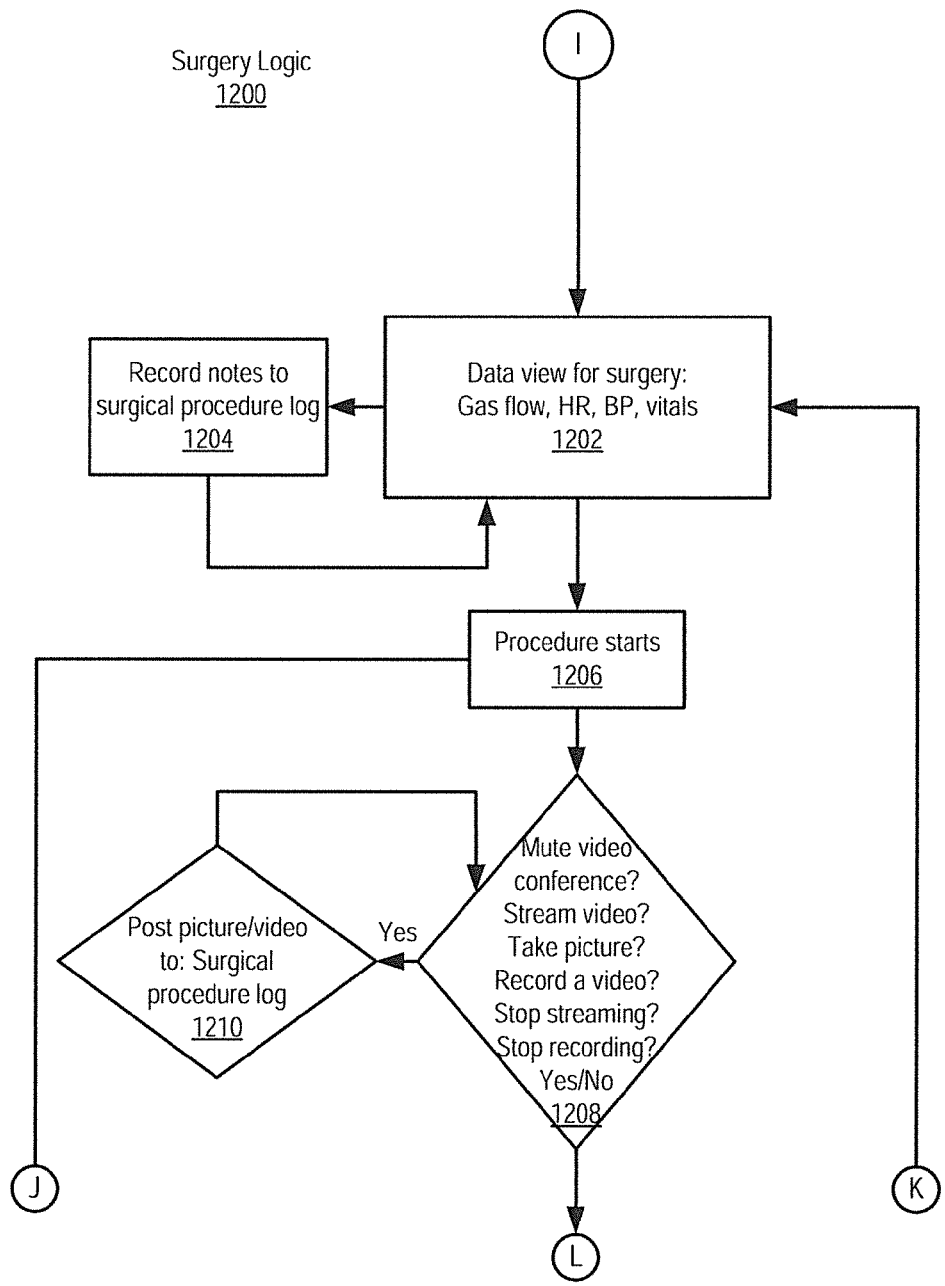
FIGS. 12A and 12B illustrate a flowchart of a surgery logic, according to an example of the present disclosure.
Figure 12B:
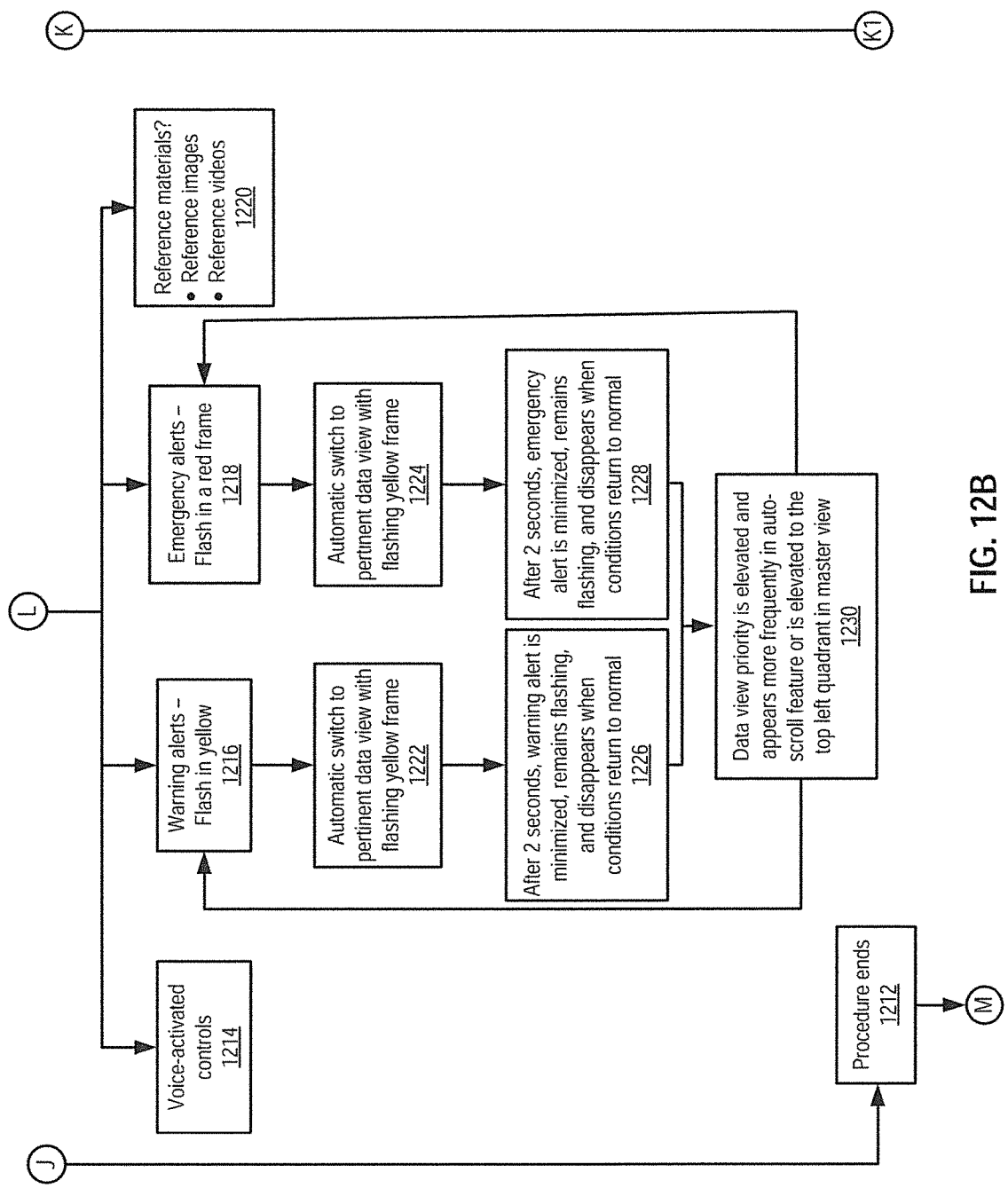

Referring to FIGS. 12A and 12B, for the surgery control logic 1200 of FIGS. 12A and 12B, the surgery control module 238 may implement the surgery control logic 1200.

At block 1202, the user 104 (e.g., a physician performing the surgery) may be provided with a data view for the surgery at the context based AR glasses 114. For example, the user 104 may be provided with a data view that includes gas flow, patient heart rate, patient blood pressure, and/or other vitals. Other specialized views may include body temperature distributions, etc. Further, patient data and the type of procedure may be accounted for in the surgery data view.

At block 1204, the user 104 may record notes related to the surgery, for example, in a surgical procedure log.

At block 1206, the surgical procedure may start.

At block 1208, the user 104 may be provided with various options during the surgery. For example, the user 104 may be provided with options to mute a video conference, stream video, take pictures, record a video, stop streaming, and/or stop recording. The options at block 1208 may be available to the user 104 at any time during the surgery.

At block 1210, the user 104 may be provided with the option to post pictures and/or videos related to the surgery in a surgical procedure log.

At block 1212, the surgical procedure may conclude.

At block 1214, following block 1208, the surgery control module 238 may initiate voice-activated controls for the context based AR glasses 114. For example, the voice-activated controls may provide for raising/lowering of oxygen levels for the patient, raising/lowering of medication levels for the patient, and/or control of other operating room (OR) equipment.

At block 1216, following block 1208, the surgery control module 238 may initiate warning alerts for the context based AR glasses 114. For example, warning alerts may flash in yellow for the context based AR glasses 114. The warning alerts may be based on the potential violation of a surgical condition related to the user 104, the patient, and/or the surgical equipment.

At block 1218, following block 1208, the surgery control module 238 may initiate emergency alerts for the context based AR glasses 114. For example, emergency alerts may flash in red for the context based AR glasses 114. Emergency alerts may include, for example, a dropping heart rate for the patient. Thus, the emergency alerts may be based on the violation of a surgical condition related to the user 104, the patient, and/or the surgical equipment.

At block 1220, following block 1208, the surgery control module 238 may provide for reference materials for the context based AR glasses 114. The reference materials may include, for example, reference images, reference videos, etc.

At blocks 1222 and 1224, following blocks 1216 and 1218, respectively, processing may switch to a pertinent data view with a flashing colored (e.g., yellow) frame.

At block 1226, following block 1222, after a predetermined time period (e.g., 2 seconds), the warning alert may be minimized. Additionally or alternatively, the warning alert may remain flashing, and/or disappear when conditions related to the warning alert return to normal.

At block 1228, following block 1224, after a predetermined time period (e.g., 2 seconds), the emergency alert may be minimized. Additionally or alternatively, the emergency alert may remain flashing, and/or disappear when conditions related to the emergency alert return to normal.

At block 1230, following blocks 1226 and 1228, the data view priority may be elevated. Further, the data view priority may appear more frequently in an auto-scroll feature with the context based AR glasses 114, or may be elevated to, for example, the top left quadrant in a master view for the context based AR glasses 114.

Figure 13:
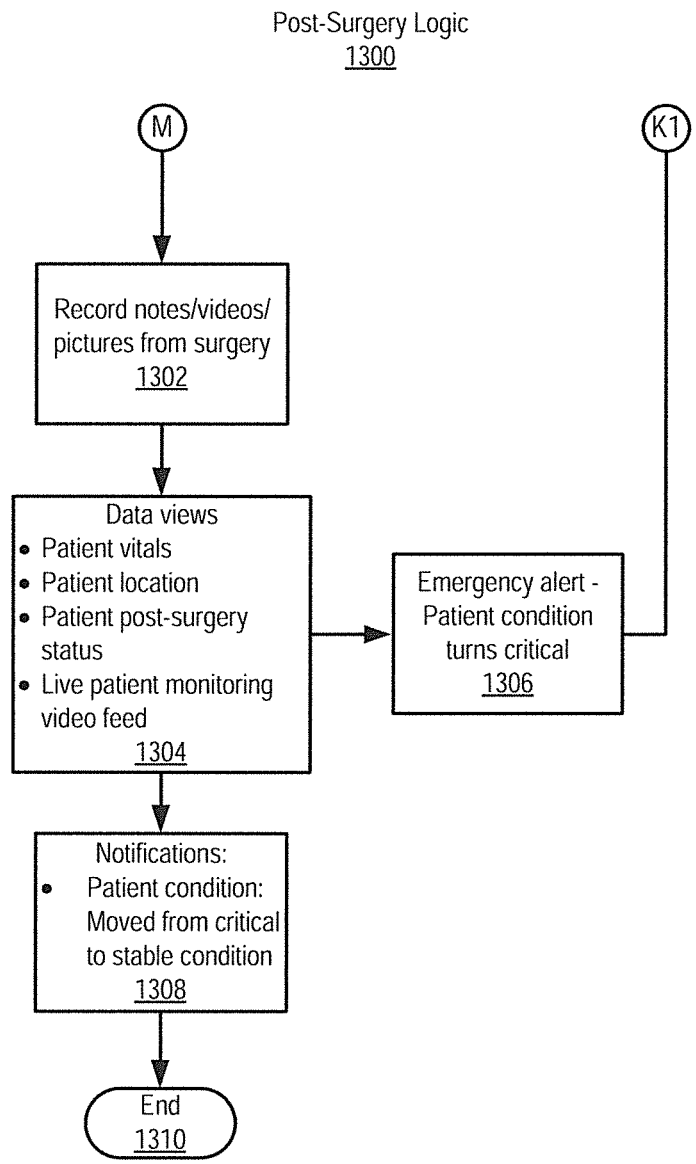
FIG. 13 illustrates a flowchart of a post-surgery logic, according to an example of the present disclosure.

Referring to FIG. 13, for the post-surgery control logic 1300 of FIG. 13, the post-surgery control module 240 may implement the post-surgery control logic 1300.

At block 1302, the user 104 (e.g., the physician that performed the surgery, or another physician responsible for post-surgery care) may be provided with the option to record notes, videos, and/or pictures from the surgery using the context based AR glasses 114.

At block 1304, for post-surgery care, the user 104 may be provided with a variety of data views including, for example, patient vitals, patient location, patient post-surgery status, and/or a live patient monitoring video feed.

At block 1306, in the event of an emergency, an emergency alert may be generated at the context based AR glasses 114. Further, processing may revert back to block 1202.

At block 1308, the user 104 may be provided with notifications, such as, for example, patient condition, and/or whether the patient has been moved, for example, from critical to stable condition.

At block 1310, processing related to the post-surgery logic 1300 may conclude.

Figure 14:
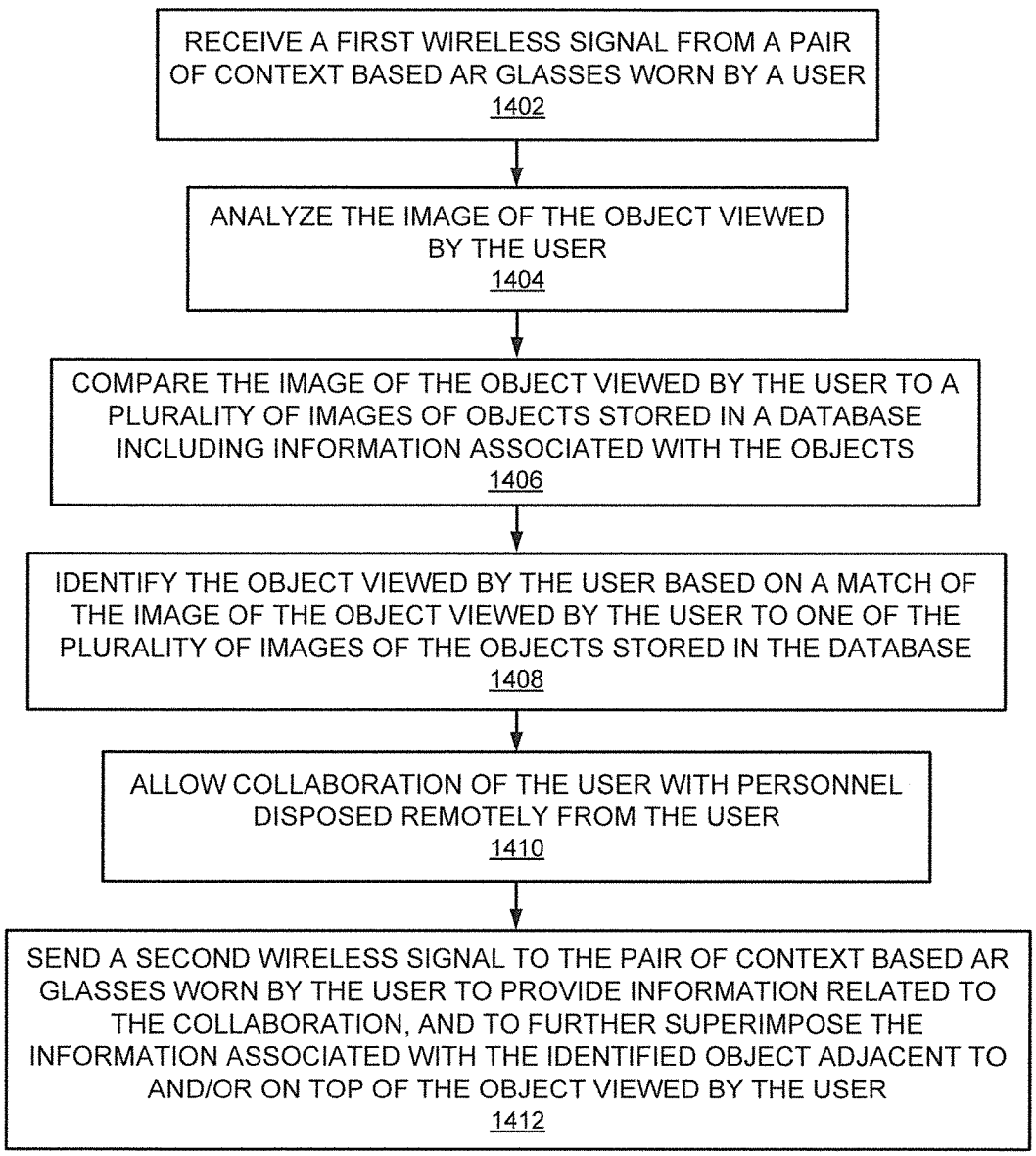
FIG. 14 illustrates a method for context based AR, according to an example of the present disclosure.
Figure 15:
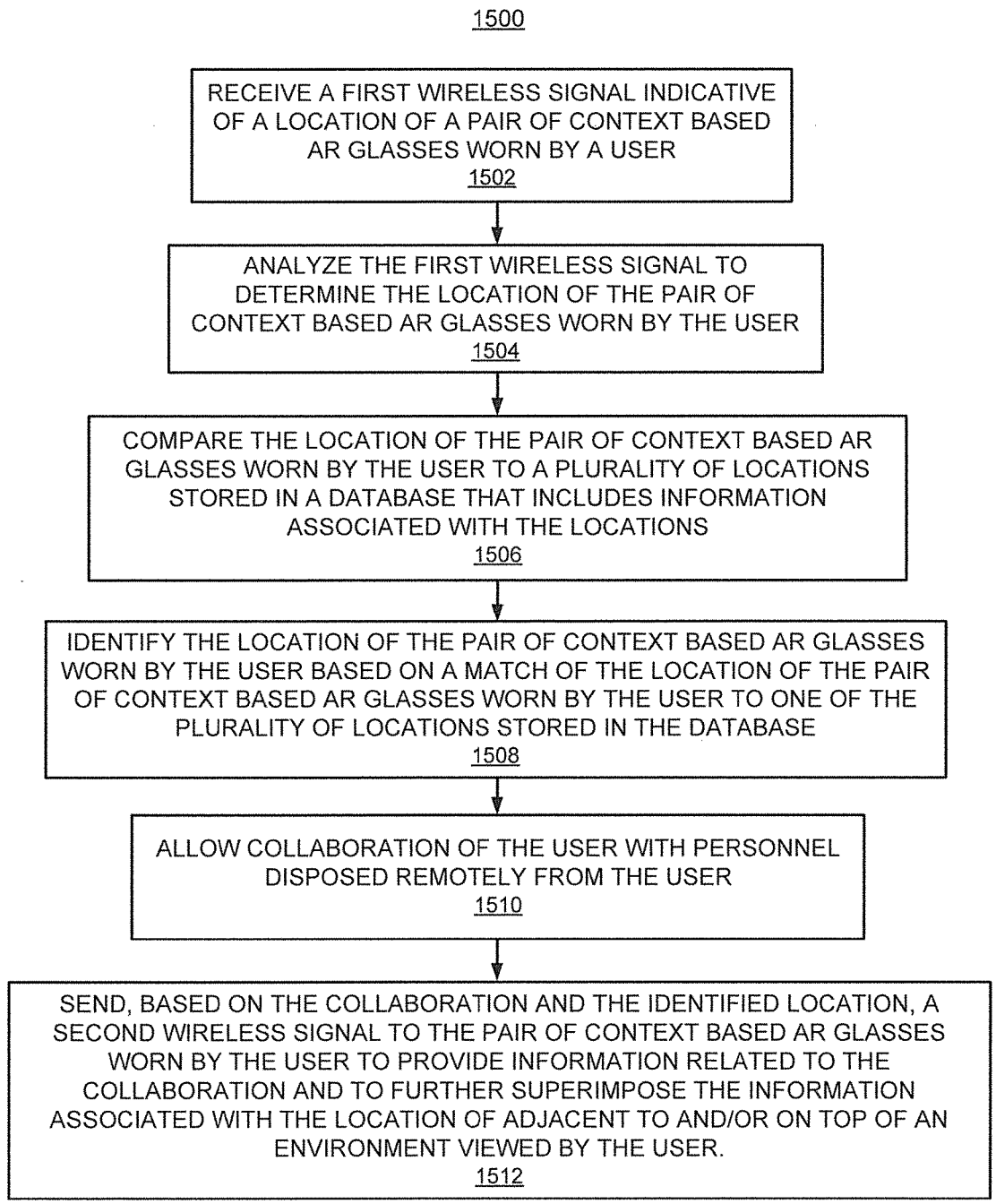
FIG. 15 illustrates further details of the method for context based AR, according to an example of the present disclosure.

FIGS. 14 and 15 respectively illustrate flowcharts of methods 1400 and 1500 for context based AR, according to examples. The methods 1400 and 1500 may be implemented on the context based AR system 102 described above with reference to FIGS. 1-13 by way of example and not limitation. The methods 1400 and 1500 may be practiced in other systems.

Referring to FIG. 14, at block 1402, the method 1400 may include receiving, for example, by the video analytics and computer vision module 204 including a processor (e.g., the processor 1602), a first wireless signal from the pair of context based AR glasses 114 worn by the user 104. The context based AR glasses 114 may include a display viewable by the user 104 and a camera to image the object 118 viewed by the user 104.

At block 1404, the method 1400 may include analyzing, for example, by the video analytics and computer vision module 204, the image of the object 118 viewed by the user 104.

At block 1406, the method 1400 may include comparing, for example, by the video analytics and computer vision module 204, the image of the object 118 viewed by the user 104 to a plurality of images of objects stored in a database (e.g., the asset database 248 and/or the user database 252) including information associated with the objects.

At block 1408, the method 1400 may include identifying, for example, by the video analytics and computer vision module 204, the object 118 viewed by the user 104 based on a match of the image of the object viewed by the user to one of the plurality of images of the objects stored in the database.

At block 1410, the method 1400 may include allowing, for example, by the collaboration integration module 202 including a processor (e.g., the processor 1602 or another processor), collaboration of the user 104 with personnel 106 disposed remotely from the user 104.

At block 1412, the method 1400 may include sending, for example, by the collaboration integration module 202, based on the collaboration and the identified object, a second wireless signal to the pair of context based AR glasses 114 worn by the user 104 to provide information related to the collaboration, and to further superimpose the information associated with the identified object adjacent to and/or on top of the object viewed by the user.

According to an example, the method 1400 may further include determining, for example, by the workflow determination module 208, a type of workflow associated with the user. The workflow determination module 208 may be operable with the collaboration integration module 202 to implement context based collaboration of the personnel 106 with the user 104 based on the type of workflow associated with the user 104. Determining a type of workflow associated with the user 104 may include determining whether the type of workflow associated with the user is a non-medical industry workflow (e.g., the workflow 300) or a medical industry workflow (e.g., the workflows 1000, 1100, 1200, and 1300).

According to an example, the method 1400 may further include implementing, for example, by the training control module 210 that is operable with the collaboration integration module 202, training functionality for the user 104 by providing the user with a step by step repair guide for the object 118 viewed by the user superimposed adjacent to and/or on top of the object viewed by the user.

According to an example, the method 1400 may further include implementing, for example, by the maintenance control module 212 that is operable with the collaboration integration module 202, maintenance functionality for the user 104 by providing the user with a maintenance history for the object 118 viewed by the user superimposed adjacent to and/or on top of the object viewed by the user.

According to an example, the method 1400 may further include implementing, for example, by the safety control module 214 that is operable with the collaboration integration module 202, safety functionality for the user 104 by providing the user with a hazard alert (e.g., a warning related to temperature, location, etc.) for the object 118 viewed by the user superimposed adjacent to and/or on top of the object viewed by the user.

According to an example, the method 1400 may further include implementing, for example, by the safety control module 214 that is operable with the collaboration integration module 202, safety functionality for the user by providing the user with an internal operation display (e.g., how liquid flows, gears move, etc.) for the object 118 viewed by the user superimposed adjacent to and/or on top of the object viewed by the user.

According to an example where the object viewed by the user is a patient, the method 1400 may further include implementing, for example, by the trauma EMT response module 234 that is operable with the collaboration integration module 202, trauma EMT response functionality for the user 104 by providing the user with vital information related to the patient viewed by the user superimposed adjacent to and/or on top of the patient viewed by the user, and/or an option to specify treatment rendered to the patient viewed by the user.

According to an example where the object viewed by the user is a patient, the method 1400 may further include implementing, for example, by the pre-surgery control module 236 that is operable with the collaboration integration module 202, pre-surgery functionality for the user 104 by providing the user with vital information related to the patient viewed by the user superimposed adjacent to and/or on top of the patient viewed by the user, and/or an option to consult with other users regarding a prognosis related to the patient viewed by the user.

According to an example where the object viewed by the user is a patient, the method 1400 may further include implementing, for example, by the surgery control module 238 that is operable with the collaboration integration module 202, surgery functionality for the user 104 by providing the user with vital information related to the patient viewed by the user superimposed adjacent to and/or on top of the patient viewed by the user, and/or alerts related to a change in a vitals status of the patient viewed by the user.

According to an example where the object viewed by the user is a patient, the method 1400 may further include implementing, for example, by the post-surgery control module 240 that is operable with the collaboration integration module 202, post-surgery functionality for the user 104 by providing the user with vital information related to the patient viewed by the user superimposed adjacent to and/or on top of the patient viewed by the user, and/or an option to record further information related to the patient's health for the patient viewed by the user.

According to an example where the context based AR glasses include a speaker, the method 1400 may further include allowing, by the collaboration integration module 202, the personnel 106 to provide audio information related to the collaboration to the user by the speaker.

Referring to FIG. 15, at block 1502, the method 1500 may include receiving, by a processor (e.g., the processor 1602), a first wireless signal indicative of a location of a pair of context based AR glasses 114 worn by a user 104.

At block 1504, the method 1500 may include analyzing the first wireless signal to determine the location of the pair of context based AR glasses worn by the user.

At block 1506, the method 1500 may include comparing the location of the pair of context based AR glasses worn by the user to a plurality of locations stored in a database (e.g., any one of the databases 242-252) the that includes information associated with the locations.

At block 1508, the method 1500 may include identifying the location of the pair of context based AR glasses 114 worn by the user 104 based on a match of the location of the pair of context based AR glasses worn by the user to one of the plurality of locations stored in the database.

At block 1510, the method 1500 may include allowing collaboration of the user with personnel 106 disposed remotely from the user 104.

At block 1512, the method 1500 may include sending, based on the collaboration and the identified location, a second wireless signal to the pair of context based AR glasses 114 worn by the user to provide information related to the collaboration and to further superimpose the information associated with the location adjacent to and/or on top of an environment 116 viewed by the user 104.

According to an example, the information associated with the location may include a map and/or a warning associated with the location.

According to an example where the context based AR glasses further include a camera to image an object 118 in the environment 116 viewed by the user, the method 1500 may further include analyzing the image of the object viewed by the user, comparing the image of the object viewed by the user to a plurality of images of objects stored in the database including information associated with the plurality of images of the objects, identifying the object viewed by the user based on a match of the image of the object viewed by the user to one of the plurality of images of the objects stored in the database, and sending, based on the collaboration, the identified object, and the identified location, the second wireless signal to the pair of context based AR glasses 114 worn by the user 104 to provide the information related to the collaboration and to further superimpose the information associated with the location and the identified object adjacent to and/or on top of the object viewed by the user.

Figure 16:
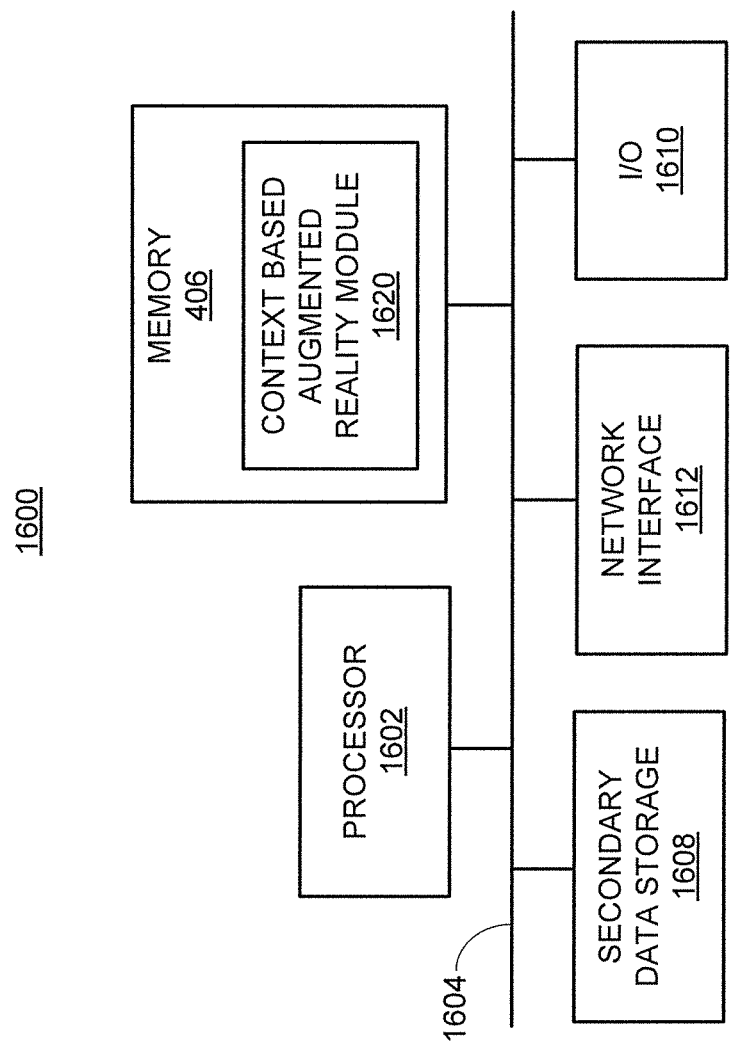
FIG. 16 illustrates a computer system, according to an example of the present disclosure.

FIG. 16 shows a computer system 1600 that may be used with the examples described herein. The computer system may represent a generic platform that includes components that may be in a server or another computer system. The computer system 1600 may be used as a platform for the system 102. The computer system 1600 may execute, by a processor (e.g., a single or multiple processors) or other hardware processing circuit, the methods, functions and other processes described herein. These methods, functions and other processes may be embodied as machine readable instructions stored on a computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory).

The computer system 1600 may include a processor 1602 that may implement or execute machine readable instructions performing some or all of the methods, functions and other processes described herein. Commands and data from the processor 1602 may be communicated over a communication bus 1604. The computer system may also include a main memory 1606, such as a random access memory (RAM), where the machine readable instructions and data for the processor 1602 may reside during runtime, and a secondary data storage 1608, which may be non-volatile and stores machine readable instructions and data. The memory and data storage are examples of computer readable mediums. The memory 1606 may include a context based AR module 1620 including machine readable instructions residing in the memory 1606 during runtime and executed by the processor 1602. The context based AR module 1620 may include the modules of the system 102 shown in FIGS. 1, 2A, and 2B.

The computer system 1600 may include an I/O device 1610, such as a keyboard, a mouse, a display, etc. The computer system may include a network interface 1612 for connecting to a network. Other known electronic components may be added or substituted in the computer system.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A context based augmented reality (AR) system comprising:
   a processor; and
   a memory storing machine readable instructions that when executed by the processor cause the processor to:
      receive a first wireless signal from a pair of context based AR glasses worn by a user, wherein the context based AR glasses include a display viewable by the user and a camera to image an object viewed by the user, wherein the object is equipment viewed by the user;
      analyze the image of the object viewed by the user;
      compare the image of the object viewed by the user to a plurality of images of objects stored in a database, wherein the database includes information associated with the plurality of images of the objects;
      based on a match of the image of the object viewed by the user to one of the plurality of images of the objects stored in the database, identify the object viewed by the user;
      determine a type of workflow associated with the user;
      implement, based on the type of workflow associated with the user, context based collaboration of the user with personnel disposed remotely from the user and out of the view of the camera;
      send, based on the context based collaboration of the user with the personnel disposed remotely from the user and based on the identified object, a second wireless signal to the pair of context based AR glasses worn by the user to provide information related to the context based collaboration of the user with the personnel disposed remotely from the user, and to further superimpose the information associated with the identified object at least one of adjacent to and on top of the object viewed by the user; and
      implement, for the user viewing an external surface of the object by the pair of context based AR glasses, safety functionality for the user by providing the user, based on the object viewed only by the pair of context based AR glasses, with a computer generated virtual internal operation display including movement of internal parts of the object viewed by the user superimposed at least one of adjacent to and on top of the object viewed by the user, wherein the movement of the internal parts is not visible to the user without the computer generated virtual internal operation display.

2. The context based AR system according to claim 1, wherein the machine readable instructions to determine a type of workflow associated with the user further comprise machine readable instructions to cause the processor to:
   determine whether the type of workflow associated with the user is a non-medical industry workflow or a medical industry workflow.

3. The context based AR system according to claim 1, wherein the machine readable instructions, when executed by the processor, further cause the processor to:
   implement training functionality for the user by providing the user with a step by step repair guide for the object viewed by the user superimposed at least one of adjacent to and on top of the object viewed by the user.

4. The context based AR system according to claim 1, wherein the machine readable instructions, when executed by the processor, further cause the processor to:
   implement maintenance functionality for the user by providing the user with a maintenance history for the object viewed by the user superimposed at least one of adjacent to and on top of the object viewed by the user.

5. The context based AR system according to claim 1, wherein the machine readable instructions, when executed by the processor, further cause the processor to:
   implement safety functionality for the user by providing the user with a hazard alert for the object viewed by the user superimposed at least one of adjacent to and on top of the object viewed by the user.

6. The context based AR system according to claim 1, wherein the movement of the internal parts includes movement of liquid or movement of gears of the object viewed by the user.

7. A method for context based augmented reality (AR), the method comprising:
   receiving a first wireless signal from a pair of context based AR glasses worn by a user, wherein the context based AR glasses include a display viewable by the user and a camera to image an object viewed by the user;
   analyzing, by a processor, the image of the object viewed by the user;
   comparing the image of the object viewed by the user to a plurality of images of objects stored in a database including information associated with the objects;
   identifying the object viewed by the user based on a match of the image of the object viewed by the user to one of the plurality of images of the objects stored in the database;
   implementing collaboration of the user with personnel disposed remotely from the user and out of the view of the camera;
   sending based on the collaboration and the identified object, a second wireless signal to the pair of context based AR glasses worn by the user to provide information related to the collaboration, and to further superimpose the information associated with the identified object at least one of adjacent to and on top of the object viewed by the user; and
   implementing, for the user viewing an external surface of the object by the pair of context based AR glasses, safety functionality for the user by providing the user, based on the object viewed only by the pair of context based AR glasses, with a computer generated virtual internal operation display including movement of internal parts of the object viewed by the user superimposed at least one of adjacent to and on top of the object viewed by the user, wherein the movement of the internal parts is not visible to the user without the computer generated virtual internal operation display.

8. The method for context based AR according to claim 7, wherein the object viewed by the user is a patient, further comprising:
   implementing trauma EMT response functionality for the user by providing the user with at least one of vital information related to the patient viewed by the user superimposed at least one of adjacent to and on top of the patient viewed by the user, and an option to specify treatment rendered to the patient viewed by the user.

9. The method for context based AR according to claim 7, wherein the object viewed by the user is a patient, further comprising:
implementing pre-surgery functionality for the user by providing the user with at least one of vital information related to the patient viewed by the user superimposed at least one of adjacent to and on top of the patient viewed by the user, and an option to consult with other users regarding a prognosis related to the patient viewed by the user.

10. The method for context based AR according to claim 7, wherein the object viewed by the user is a patient, further comprising:
implementing surgery functionality for the user by providing the user with at least one of vital information related to the patient viewed by the user superimposed at least one of adjacent to and on top of the patient viewed by the user, and alerts related to a change in a vitals status of the patient viewed by the user.

11. The method for context based AR according to claim 7, wherein the object viewed by the user is a patient, further comprising:
implementing post-surgery functionality for the user by providing the user with at least one of vital information related to the patient viewed by the user superimposed at least one of adjacent to and on top of the patient viewed by the user, and an option to record further information related to the patient's health for the patient viewed by the user.

12. The method for context based AR according to claim 7, wherein the context based AR glasses include a speaker, the method further comprising:
allowing the personnel to provide audio information related to the collaboration to the user by the speaker.

13. A non-transitory computer readable medium having stored thereon machine readable instructions for context based augmented reality (AR), the machine readable instructions when executed cause a computer system to:
receive, by a processor, a first wireless signal indicative of a location of a pair of context based AR glasses worn by a user, wherein the context based AR glasses include a display viewable by the user;
analyze the first wireless signal to determine the location of the pair of context based AR glasses worn by the user;
compare the location of the pair of context based AR glasses worn by the user to a plurality of locations stored in a database, wherein the database includes the plurality of locations and information associated with the locations;
identify the location of the pair of context based AR glasses worn by the user based on a match of the location of the pair of context based AR glasses worn by the user to one of the plurality of locations stored in the database;
determine a type of workflow associated with the user;
implement, based on the type of workflow associated with the user, context based collaboration of the user with personnel disposed remotely from the user and out of a view of a camera of the pair of context based AR glasses worn by the user;
send, based on the context based collaboration of the user with the personnel disposed remotely from the user and based on the identified location, a second wireless signal to the pair of context based AR glasses worn by the user to provide information related to the context based collaboration of the user with the personnel disposed remotely from the user and to further superimpose the information associated with the location at least one of adjacent to and on top of an environment viewed by the user, wherein the context based AR glasses include the camera to image an object in the environment viewed by the user; and
implement, for the user viewing an external surface of the object by the pair of context based AR glasses, safety functionality for the user by providing the user, based on the object viewed only by the pair of context based AR glasses, with a computer generated virtual internal operation display including movement of internal parts of the object viewed by the user superimposed at least one of adjacent to and on top of the object viewed by the user, wherein movement of the internal parts is not visible to the user without the computer generated virtual internal operation display.

14. The non-transitory computer readable medium according to claim 13, wherein the context based AR glasses use at least one of Wi-Fi, cell towers, and a global positioning system (GPS) to determine the location of the pair of context based AR glasses worn by the user.

15. The non-transitory computer readable medium according to claim 13, wherein the information associated with the location includes at least one of a map and a warning associated with the location.

16. The non-transitory computer readable medium according to claim 13, further comprising machine readable instructions to:
analyze the image of the object viewed by the user;
compare the image of the object viewed by the user to a plurality of images of objects stored in the database, wherein the database includes information associated with the plurality of images of the objects;
identify the object viewed by the user based on a match of the image of the object viewed by the user to one of the plurality of images of the objects stored in the database; and
send, based on the context based collaboration, the identified object, and the identified location, the second wireless signal to the pair of context based AR glasses worn by the user to provide the information related to the context based collaboration and to further superimpose the information associated with the location and the identified object at least one of adjacent to and on top of the object viewed by the user.

17. The non-transitory computer readable medium according to claim 13, wherein the machine readable instructions to implement the context based collaboration of the user with the personnel disposed remotely from the user, further comprises machine readable instructions to:
determine whether the type of workflow associated with the user is a non-medical industry workflow or a medical industry workflow.

18. The non-transitory computer readable medium according to claim 13, wherein the context based AR glasses include a speaker, further comprising machine readable instructions to:
allow the personnel to provide audio information related to the context based collaboration to the user by the speaker.

19. The non-transitory computer readable medium according to claim 13, further comprising machine readable instructions to:
    implement training functionality for the user by providing the user with a step by step repair guide for the object viewed by the user superimposed at least one of adjacent to and on top of the object viewed by the user.

20. The non-transitory computer readable medium according to claim 13, further comprising machine readable instructions to:
    implement maintenance functionality for the user by providing the user with a maintenance history for the object viewed by the user superimposed at least one of adjacent to and on top of the object viewed by the user.

* * * * *